(12) United States Patent
Weber et al.

(10) Patent No.: US 12,558,565 B2
(45) Date of Patent: Feb. 24, 2026

(54) LIGHT APPLICATOR SYSTEM WITH PRE-PIERCING AID

(71) Applicant: Richard Wolf GmbH, Knittlingen (DE)

(72) Inventors: Bernd Claus Weber, Karlsruhe (DE); Stephan Sieber, Knittlingen-Freudenstein (DE)

(73) Assignee: RICHARD WOLF GMBH, Knittlingen (DE)

( * ) Notice: Subject to any disclaimer, the term of this patent is extended or adjusted under 35 U.S.C. 154(b) by 226 days.

(21) Appl. No.: 18/559,616

(22) PCT Filed: May 10, 2022

(86) PCT No.: PCT/DE2022/200098
§ 371 (c)(1),
(2) Date: Nov. 8, 2023

(87) PCT Pub. No.: WO2022/237944
PCT Pub. Date: Nov. 17, 2022

(65) Prior Publication Data
US 2024/0238610 A1 Jul. 18, 2024

(30) Foreign Application Priority Data
May 14, 2021 (DE) .................... 10 2021 204 909.5

(51) Int. Cl.
*A61N 5/06* (2006.01)

(52) U.S. Cl.
CPC .......... *A61N 5/062* (2013.01); *A61N 5/0601* (2013.01); *A61N 2005/0612* (2013.01); *A61N 2005/0643* (2013.01)

(58) Field of Classification Search
CPC ................. A61N 5/062; A61N 5/0601; A61N 2005/0612; A61N 2005/063;
(Continued)

(56) References Cited

U.S. PATENT DOCUMENTS 6,048,359 A * 4/2000 Biel ...................... A61N 5/0601
606/2
8,679,103 B2 * 3/2014 Krespi ................... A61B 18/26
606/2
(Continued)

FOREIGN PATENT DOCUMENTS

DE 10300787 A1 9/2004
DE 102019129556 A1 * 5/2021 ........... A61B 5/0084
(Continued)

*Primary Examiner* — Ahmed M Farah
(74) *Attorney, Agent, or Firm* — McGlew and Tuttle, P.C.

(57) ABSTRACT

A light applicator system (19), for organic body (9) examination and/or treatment, includes a light applicator (1) with a distal-side insertion portion (13) with an actively light-emitting element and a needle tip (25) for piercing tissue (11) arranged axially centrally at the distal end. A positioning element (5) is fixable relative to the organic body and has a receptacle (3) for a light applicator defined position and orientation and in which the needle tip is guided axially centred. A pre-piercing aid (21) has a pre-piercing aid shaft (23) and an axially centrally arranged distal needle tip (15). The pre-piercing aid fits into the receptacle such that the needle tip is guided axially centred in the receptacle, and the pre-piercing aid has a defined orientation with respect to the organic body which corresponds to the defined orientation with respect to the organic body of the at least one light applicator.

18 Claims, 19 Drawing Sheets

(58) Field of Classification Search
CPC .... A61N 2005/0632; A61N 2005/0643; A61N
2005/0651
USPC .......................................................... 607/88
See application file for complete search history.

(56) References Cited

U.S. PATENT DOCUMENTS

| 12,296,186 | B2 * | 5/2025 | Weber ...................... A61N 5/06 |
| 12,318,625 | B2 * | 6/2025 | Weber .................... A61N 5/062 |
| 2008/0249517 | A1 * | 10/2008 | Svanberg ............. A61N 5/0601 |
| | | | 606/15 |
| 2010/0049178 | A1 * | 2/2010 | Deem ................ A61B 18/1477 |
| | | | 606/1 |
| 2012/0041521 | A1 | 2/2012 | Oron et al. |
| 2019/0002594 | A1 | 1/2019 | Hode et al. |

FOREIGN PATENT DOCUMENTS

| EP | 0221315 | A1 | 5/1987 |
| GB | 2514444 | A | 11/2014 |

* cited by examiner

LIGHT APPLICATOR SYSTEM WITH PRE-PIERCING AID

CROSS REFERENCE TO RELATED APPLICATIONS

This application is a United States National Phase Application of International Application PCT/DE2022/200098, filed May 10, 2022, and claims the benefit of priority under 35 U.S.C. § 119 of German Application 10 2021 204 909.5, filed May 14, 2021, the entire contents of which are incorporated herein by reference.

TECHNICAL FIELD

The present disclosure relates to a light applicator system for examination and/or treatment of an organic body, in particular for photodynamic therapy (PDT) of pathological tissue.

BACKGROUND

It is known to use endoscopes to make video recordings of the inside of a human or animal body for the purpose of medical diagnosis and/or therapy. It is a constant endeavor here to make the insertion portion of endoscopes as thin as possible so that the smallest possible cavities can be viewed and the tissue is only minimally affected.

However, endoscopes are not only used to take pictures or make video recordings, but are also used as diagnostic or therapeutic tools themselves. For example, fluorescence endoscopy can be used for the detection and localization of pre-malignant and early malignant tissue; this does not require a natural true-color representation of the tissue, but only fluorescence excitation, which can be used to distinguish pathological tissue from healthy tissue. The pathological tissue itself or an accumulation of bacteria indicating pathological tissue can be specifically fluoresced by means of light radiation and thus can be recognizably localized compared to the surrounding healthy tissue. Fluorescence endoscopy can be carried out, for example, as part of photodynamic diagnosis (PDD) and/or photodynamic therapy (PDT) using a photosensitizer or marker substance that selectively accumulates on pathological tissue.

In photodynamic therapy (PDT), light is applied directly to or even into pathological tissue by means of a light applicator in order to promote the light-induced formation of oxygen radicals by means of the locally enriched photosensitizer or marker substance and thereby destroy the pathological tissue, such as a tumor. Typically, laser light is coupled into a light guide and directed to the tissue. If the pathological tissue is located on an outer surface, e.g. the skin, or an inner surface, e.g. the inner surface of the esophagus or intestinal wall, then the therapy light can be coupled out relatively easily and beamed onto the pathological tissue surface. However, if the pathological tissue extends over a volume, it is not always possible to effectively irradiate a tumor from "outside" due to the limited penetration depth of the light into the tissue. In this case, PDT is particularly effective if the light is emitted as isotropically as possible from inside the pathological tissue volume. For this purpose, the light applicator must be pierced into the pathological tissue. This is also called interstitial PDT (through internal surfaces) and/or percutaneous PDT (through the skin).

For example, U.S. Pat. No. 6,048,359 describes how multiple light applicators are inserted into pathological tissue using a positioning grid.

However, it has turned out to be a technical challenge with the known solutions that piercing the skin with a very thin and long light applicator in some cases requires such a high manual force that the light applicator bends and the deeper-lying target tissue is therefore missed. This problem exists in particular when the target tissue is located relatively far inside the body, i.e. the light applicator must be relatively long but as thin as possible in order to make the piercing as minimally invasive as possible.

This results in the problem of providing a light applicator system with which deep-lying tissue in an organic body can be reached as precisely and minimally invasively as possible for examination and/or treatment.

SUMMARY

According to the present disclosure, a light applicator system for examination and/or treatment of an organic body is provided for solving this problem, wherein the light applicator system comprises at least one light applicator and a positioning element, wherein the light applicator comprises a distal-side insertion portion with at least one actively light-emitting element, e.g. an LED, and a needle tip which is arranged axially centrally in relation to the insertion portion of the light applicator at the distal end for piercing tissue of the organic body, wherein the positioning element can be fixed at least temporarily in a defined position and orientation relative to the organic body and has at least one receptacle for the at least one light applicator, in which the at least one light applicator has, at least temporarily, a defined position and orientation with respect to the organic body, and in which the needle tip of the light applicator is guided axially centred with respect to the at least one receptacle of the positioning element, wherein the light applicator system has a pre-piercing aid, wherein the pre-piercing aid has a needle tip arranged axially centrally with respect to the pre-piercing aid shaft and also fits into the at least one receptacle of the positioning element in such a way that the needle tip of the pre-piercing aid, with respect to the at least one receptacle of the positioning element, is also guided axially centred in this receptacle and that the pre-piercing aid has, at least temporarily, a defined orientation with respect to the organic body which corresponds to the defined orientation with respect to the organic body of the at least one light applicator. This ensures that the needle tip of the light applicator finds the small opening created in advance by the needle tip of the pre-piercing aid in the patient's skin by itself or "automatically" by merely inserting the light applicator into the at least one receptacle of the positioning element and moving it forward in the distal direction within this receptacle. Thus, the operator does not have to search for the small pre-pierced skin opening and does not need manual skill to hit it. The pre-piercing reduces the resistance caused by the tough skin that the applicator experiences when inserted or advanced into or through the skin, thereby reducing the risk of bending the light applicator or its insertion portion so that the needle tip of the light applicator reaches the target point in the organic body.

In the case of the light applicator disclosed here, preferably no laser light guide is used, but rather the diagnostic or therapeutic light is generated in situ at the distal end of the light applicator by an actively light-emitting element, e.g. a miniaturised LED, for example with a lateral width of less than 1 mm. An "actively" light-emitting element shall be understood here to mean merely a light-emitting element that absorbs electrical energy and converts it into light, i.e. not a light guide that merely passes light onwards and/or decouples it. An expensive laser is therefore not needed in the case of an actively light-emitting element, and so costs are greatly reduced. The light applicator disclosed herein can be manufactured very cheaply and can thus be realised as a sterile disposable article for single use, making costly cleaning and sterilisation by the user obsolete. In the case of larger tumours or entire pathological organs or organ areas, the light applicator system can have a plurality of light applicators that are used simultaneously for PDT by piercing the organ with them in a manner distributed over the entire organ in order to homogeneously illuminate the entire organ. Since the photosensitiser or marker substance selectively accumulates only in pathological tissue and reacts there under the influence of light and the applied light quantities are relatively low, healthy tissue is not damaged by the light. On the one hand, the pathological tissue then no longer needs to be localised so precisely beforehand and on the other hand, the risk of pathological tissue remaining unnoticed and untreated is reduced.

Preferably, the insertion portion of the light applicator has a needle tip arranged at least partially distally from the LED and tapering distalwards with a light-transparent scattering body for scattering the light of the LED. The needle tip of the insertion portion of the light applicator serves, on the one hand, to make the insertion as minimally invasive as possible and, on the other hand, to scatter the light of the LED as isotropically and/or homogeneously as possible over as large a solid angle as possible, e.g. over $3\pi$.

For percutaneous PDT with multiple light applicators, it may be useful for the positioning element to have a plurality of receptacles and to form an organ-specific template that can be placed and/or adhered closely or directly in a defined manner on or to the patient's skin in order to indicate to a user insertion sites, angles and/or depths for the light applicators and to achieve the most complete and largely homogeneous illumination of the organ.

However, the light applicator can be used not only for therapy, but also for examination, i.e. diagnosis. Especially in combination with an endoscope or with the light applicator as part of an endoscope, the fluorescence produced by the light applicator of a photosensitiser or marker substance enriched in pathological tissue can be observed.

The pre-piercing aid allows the skin to be pre-pierced prior to the actual piercing of the light applicator, thereby significantly reducing the resistance caused by the skin during the actual piercing of the light applicator. Preferably, the skin is not only pre-pierced by the pre-piercing aid, but also widened and/or incised by the pre-piercing, whereby not only the initial resistance to the penetration of the light applicator is reduced, but also the subsequent frictional resistance at the light applicator when penetrating the skin. Preferably, however, the pre-piercing aid or its needle tip is designed in such a way that the pre-piercing is as atraumatic and minimally invasive as possible, so that the opening in the skin after the pre-piercing aid has been withdrawn from the skin is only very small, which on the one hand represents a great challenge for the subsequent finding and precise hitting of this opening with the light applicator or its needle tip, but on the other hand is often sufficient to reduce the resistance generated by the skin during the insertion of the light applicator.

Optionally, the light applicator system can also have a stop that defines a maximum pre-piercing depth of the pre-piercing aid. This has the advantage that the pre-piercing aid is not accidentally pierced too deep.

In a first embodiment of the light applicator system, the pre-piercing aid can preferably be a component separate from the light applicator, which can be removed from the at least one receptacle of the positioning element after a pre-piercing into the organic body, in order to subsequently introduce the light applicator through the at least one receptacle of the positioning element into the pre-pierced organic body for examination and/or treatment of the organic body.

The pre-piercing aid can be designed here to be more flexurally rigid than the light applicator, as the pre-piercing aid can be shorter and/or thicker than the light applicator.

Optionally, the pre-piercing aid can have a pre-piercing aid shaft with an axial length and diameter defining a first length-to-diameter ratio, and the light applicator insertion portion can have an axial length and diameter defining a second length-to-diameter ratio, wherein the second length-to-diameter ratio is substantially greater than the first length-to-diameter ratio. As a result, the pre-piercing aid can be configured to be substantially more flexurally rigid than the insertion portion of the light applicator. In addition, the flexural rigidity of the pre-piercing aid can be optimised with regard to the choice of material, e.g. by a solid, hard steel core, which may not always be possible with the light applicator due to additional, different requirements (for example, soft copper core for good heat conduction from the distal actively light-emitting element in the proximal direction).

Optionally, the needle tip of the pre-piercing aid can have at least one or more cutting edges, whereby the pre-pierced skin is incised, reducing the skin tension and thus the resistance caused by the skin as the insertion portion of the light applicator is pierced through.

Optionally, at least one of these cutting edges can be designed as a distally protruding cutting blade, which can simplify the incision of the skin and/or produce an even cleaner cut.

Regardless of the design in respect of optional cutting edges or cutting blades, the needle tip of the pre-piercing aid or tip thereof is always arranged axially centrally in relation to the pre-piercing aid shaft. Likewise, the needle tip of the light applicator or its tip is always arranged axially centrally in relation to the insertion portion of the light applicator.

Optionally, the pre-piercing aid may have a pre-piercing aid shaft with a diameter identical to the diameter of the insertion portion of the light applicator, and both fit precisely into an inner diameter of the at least one receptacle of the positioning element. The greater flexural rigidity of the pre-piercing aid shaft required compared to the insertion portion of the light applicator is achieved by making the pre-piercing aid shaft shorter. Preferably, the needle tip of the pre-piercing aid is provided with at least one cutting edge or cutting blade. The at least one edge or blade can be used to incise the skin during pre-piercing so that the skin offers less resistance when the light applicator is pierced through.

Optionally, the pre-piercing aid may comprise a pre-piercing aid shaft having a diameter that fits precisely into an inner diameter of the at least one receptacle of the positioning element and is larger than a diameter of the insertion portion of the light applicator, the light applicator system further comprising an adapter sleeve having an inner diameter that fits precisely into the diameter of the insertion portion of the light applicator and having, at least in portions, an outer diameter that fits precisely into an inner diameter of the at least one receptacle of the positioning element. The thicker pre-piercing aid shaft allows the skin to be stretched during pre-piercing so that it offers less resistance when the light applicator is pierced through. Optionally, the adapter sleeve can act as a protective sleeve for a needle tip of the insertion portion of the light applicator and can be coupled to the insertion portion in an axially movable and captive manner.

Optionally, the pre-piercing aid can be designed in such a way that it is inserted into the receptacle of the positioning element in conjunction with an adapter sleeve which acts as a protective sleeve for the needle tip of the pre-piercing aid, wherein the inner diameter of the adapter sleeve corresponds exactly to the diameter of the insertion portion of the pre-piercing aid and has, at least in portions, an outer diameter which fits precisely into an inner diameter of the at least one receptacle of the positioning element. If the needle tip of the pre-piercing aid is then formed, for example, with sharp cutting edges or even with a cutting blade, the skin can be incised during the pre-piercing so that it offers less resistance when the light applicator pierces through it.

Optionally, both the light applicator and the pre-piercing aid may be designed in such a way that they are inserted into the receptacle of the positioning element in conjunction with an adapter sleeve which acts as a protective sleeve for the respective needle tip, wherein the adapter sleeve of the light applicator is identical to the adapter sleeve of the pre-piercing aid at least in terms of outer and inner diameter, but possibly even completely identical.

In an alternative second embodiment of the invention, the pre-piercing aid is integrated into the light applicator, wherein the needle tip of the pre-piercing aid is a needle tip of the light applicator which is arranged at least partially distally from the LED and tapers distalwards to a point and has a light-transparent scattering body for scattering the light of the LED, wherein the stop can be positioned and/or shaped in such a way that it defines a maximum pre-piercing depth of the light applicator in a stop position and permits a greater piercing depth of the light applicator in a non-stop position. The needle tip of the light applicator thus forms the needle tip of the pre-piercing aid here and the insertion portion of the light applicator forms the pre-piercing aid shaft. Preferably, the stop of the pre-piercing aid is formed by a stabilisation sleeve that can be positioned and fixed axially on the insertion portion of the light applicator.

Regardless of whether the pre-piercing aid is a separate component or is integrated into the light applicator, the pre-piercing aid may optionally have a stabilisation sleeve in any case, which preferably forms the stop and is axially movable on a pre-piercing aid shaft of the pre-piercing aid and can be fixed in a selectable axial position on the pre-piercing aid shaft. This allows the pre-piercing depth to be adapted to the application. If the pre-piercing aid is integrated in the light applicator, the stabilisation sleeve can additionally function as an adapter sleeve and/or protective sleeve of a needle tip of the insertion portion of the light applicator or can be designed as a separate component. The stabilisation sleeve can stabilise the thin insertion portion of the light applicator proximally of the positioning element and thus make it more flexurally rigid for the pre-piercing through the skin.

Optionally, the pre-piercing aid and/or the light applicator can have a handle element on the proximal side for manual positioning and orientation. In the embodiment with integrated pre-piercing aid, there is preferably only one handle element. However, in the embodiment with a separate pre-piercing aid, there can also be only one handle element, if this is feasibly appropriately attachable to both a proximal end of the insertion portion and a proximal end of the pre-piercing aid. Alternatively, the pre-piercing aid and the light applicator can each have their own handle element. Optionally, the axial position of the pre-piercing aid and/or the insertion portion relative to the positioning element can be manually adjustable by positioning the handle element in the axial direction.

Optionally, the handle element can form the stop and be axially movable on the pre-piercing aid and/or the insertion portion and fixable in a selectable axial position. Then the handle element for the pre-piercing through the skin can be pushed distalwards until it abuts the positioning element. The pre-piercing aid can then be very short and correspondingly flexurally rigid.

Optionally, the light applicator system may have a resistance component that exerts a proximal resistance force against a force applied distally manually to the pre-piercing aid up to a maximum resistance force and abruptly releases the pre-piercing aid distalwards as soon as the distal manual force on the pre-piercing aid exceeds the maximum resistance force. This is particularly advantageous if the skin yields relatively far distalwards and the reaction force applied by the skin and directed proximalwards remains so small for a relatively long time that skin is only dented, but the pressure of the needle tip of the pre-piercing aid is not sufficient to pierce the skin. In this case, if the pre-piercing aid has not yet been struck, the skin can stretch over a relatively large distal distance with a slowly increasing reaction force and then, when the pressure of the needle tip of the pre-piercing aid for piercing through the skin is reached, can abruptly snap back proximalwards. The needle tip of the pre-piercing aid may then have already penetrated too far through the skin into underlying tissue, which is to be avoided in order to make the pre-piercing as minimally invasive as possible. This problem is made more difficult by the fact that the positioning element, for example in the form of a piercing template stuck to the skin, can block the operator's view of the needle tip and the skin.

To solve this problem, the resistance component from the skin takes over the function of building up a reaction force to build up the necessary pressure on the skin for the pre-piercing. As soon as the operator has increased the manual distal force to such an extent that the maximum resistance force is exceeded, the pre-piercing aid suddenly experiences a distal force impact with corresponding acceleration in order to apply the necessary pressure to the skin for the pre-piercing. Preferably, the needle tip of the pre-piercing aid hits the skin with a velocity and penetrates it, as it cannot yield so quickly due to its inertia and in conjunction with the underlying tissue. The stop then stops the pre-piercing aid to prevent a pre-piercing that is too deep.

Optionally, the resistance component can be at least partially elastically resiliently deformable and tensionable by the distal manual force.

Optionally, the resistance component may comprise at least one substantially axially extending spring leg with foot, wherein the foot is radially pushed away under tension of the spring leg by the distal manual force and snaps back with abrupt relaxation of the spring leg when the maximum resistance force is exceeded.

The terms "distally" and "proximally" are intended herein to mean a relative position that is distal or proximal, respectively, to a user of the system as a reference position. The terms "distal-side" and "proximal-side" are herein intended to mean, respectively, positions on a distal and proximal side of an object. The terms "distalwards" and "proximalwards" are intended herein to mean directions extending in a distal sense and proximal sense, respectively.

The disclosure is explained in greater detail below with reference to exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
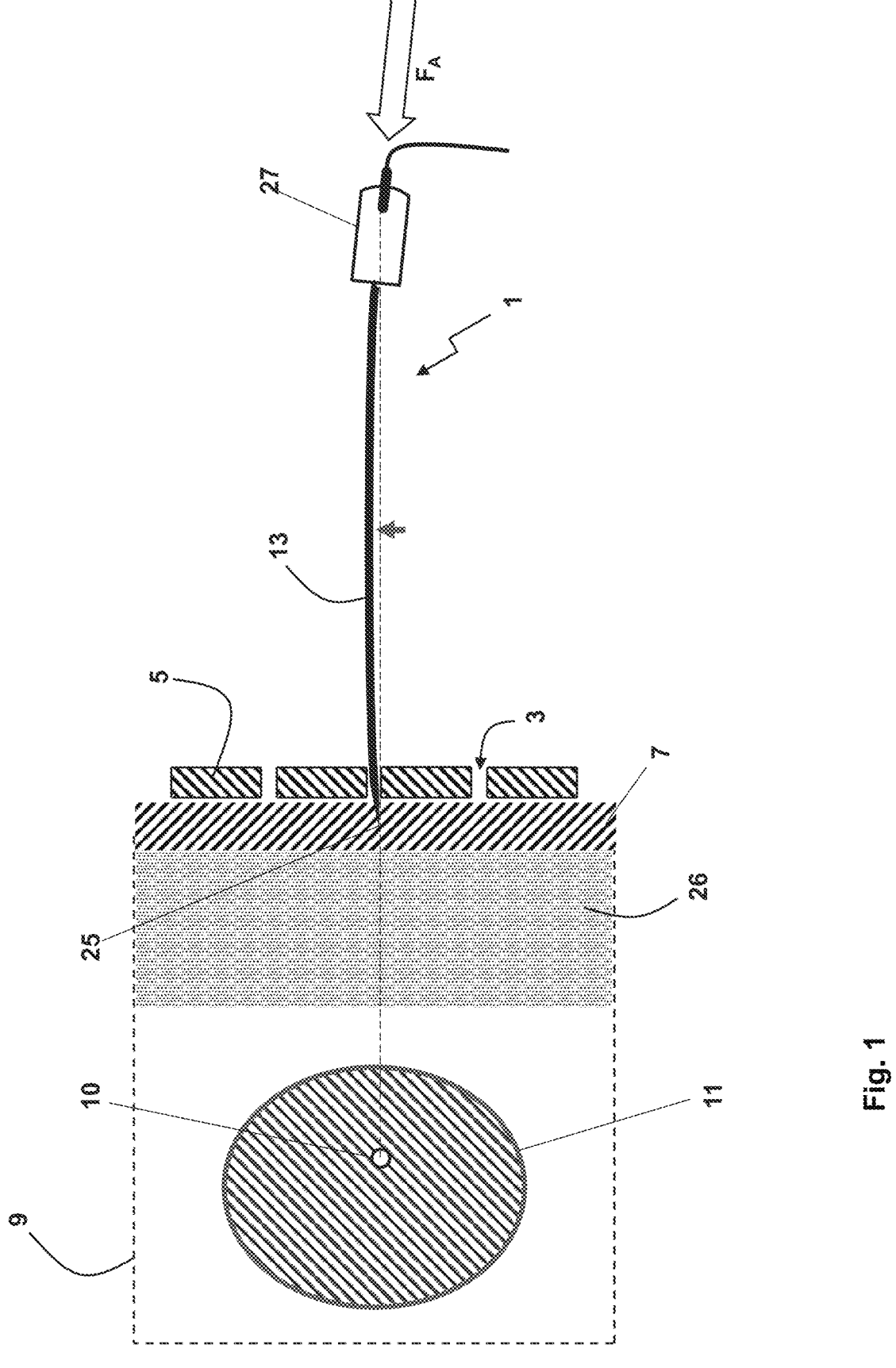
FIG. 1 is a schematic longitudinal sectional view showing a state during the piercing of an exemplary embodiment of the light applicator disclosed herein into the skin of a patient with a positioning element placed against the skin.

Referring to the drawings, FIG. 1 illustrates the problem solved by the light applicator system disclosed herein. FIG. 1 shows a light applicator 1 which is pierced into the skin 7 of an organic body 9 through a receptacle 3 of a positioning element 5. The positioning element 5 is, for example, a piercing template which is glued to the skin 7 in such a positioned manner that, with a piercing through the receptacle 3, which is formed as an opening or hole in the piercing template, a precise target point 10 in the target tissue 11 in the organic body 9 is reached with the light applicator 1. The target tissue 11 can be, for example, a tumour in an organ or the whole organ, for example the prostate. The positioning element 5 can have several receptacles 3, as shown here, in order to provide several piercing possibilities and/or so as to be able to use several light applicators 1 simultaneously.

A distal end of an insertion portion 13 of the light applicator 1 is to be pierced here into the target tissue 11 for photodynamic therapy (PDT) or diagnosis (PDD) in order to irradiate this target tissue 11 with light. For this purpose, the distal end of the insertion portion 13 has an actively light-emitting element in the form of an LED (not shown here), the main radiation direction of which is directed in the longitudinal direction of the insertion portion 13. At least partially distally of the LED, there is arranged a needle tip 25 tapering distalwards to a point, which has a light-transparent scattering body for scattering the light of the LED. The needle tip 25 is formed here substantially in one piece from the light-transparent scattering body, which may for example comprise plastic with reinforcing elements.

The insertion portion 13 of the light applicator 1 is designed to be as thin (with a diameter of 1 mm or less) and rigid as possible for the most minimally invasive treatment or diagnosis. However, the insertion portion 13 of the light applicator 1 must be made relatively long to reach target tissue 11 located relatively deep in the organic body 9. This limits the flexural rigidity achievable for the insertion portion 13 of the light applicator 1. Even if a very rigid, tubular shaft material is used, for example steel, the insertion portion 13 of the light applicator 1 can be bent manually when piercing the skin 7.

This problem is shown in FIG. 1. The skin 7 may be very leathery and tough, so that even with a very pointed needle tip 25, the manual force FA to be applied by the operator to push a handle element 27 of the light applicator 1, which is arranged proximally on the insertion portion 13 of the light applicator 1, distally is relatively large. This may cause the insertion portion 13 of the light applicator 1 to bend as shown. However, such bending is problematic, even if it is relatively small, as it may cause the needle tip 25 to miss the target point 10 in the deep target tissue 11. Since the penetration depth of the light into the tissue is not very deep, depending on the wavelength used, and thus only a relatively small tissue volume can be irradiated, several light applicators 1 may have to be positioned precisely at a respective target point 10 in the target tissue 11 in order to cover the entire volume of the target tissue 11 in the sum of the irradiated tissue volumes. However, bending the insertion portion 13 of the light applicator 1 as shown in FIG. 1 does not ensure precise positioning at the target point 10 in the target tissue 11.

Figure 2:
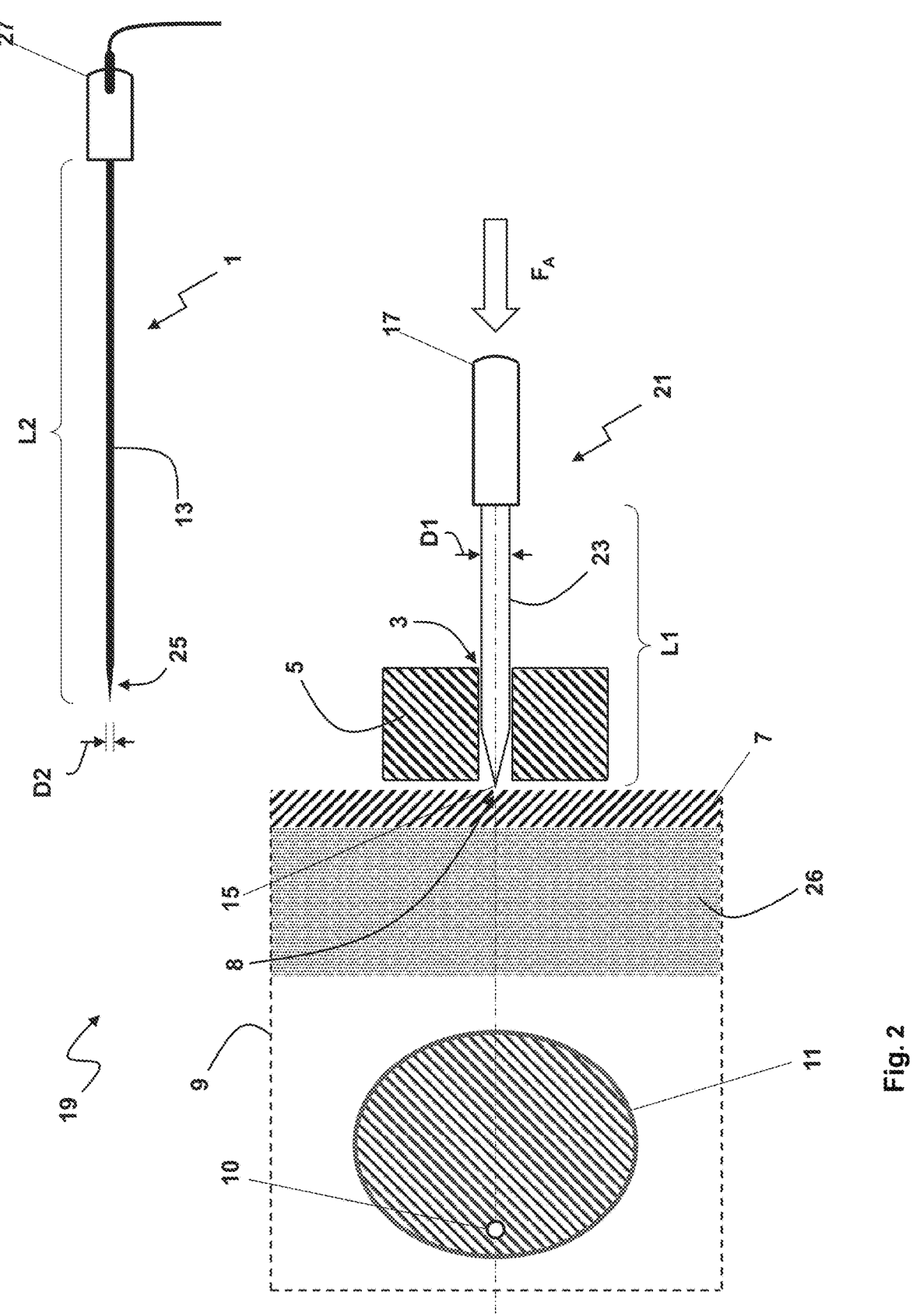
FIG. 2.
Figure 3:
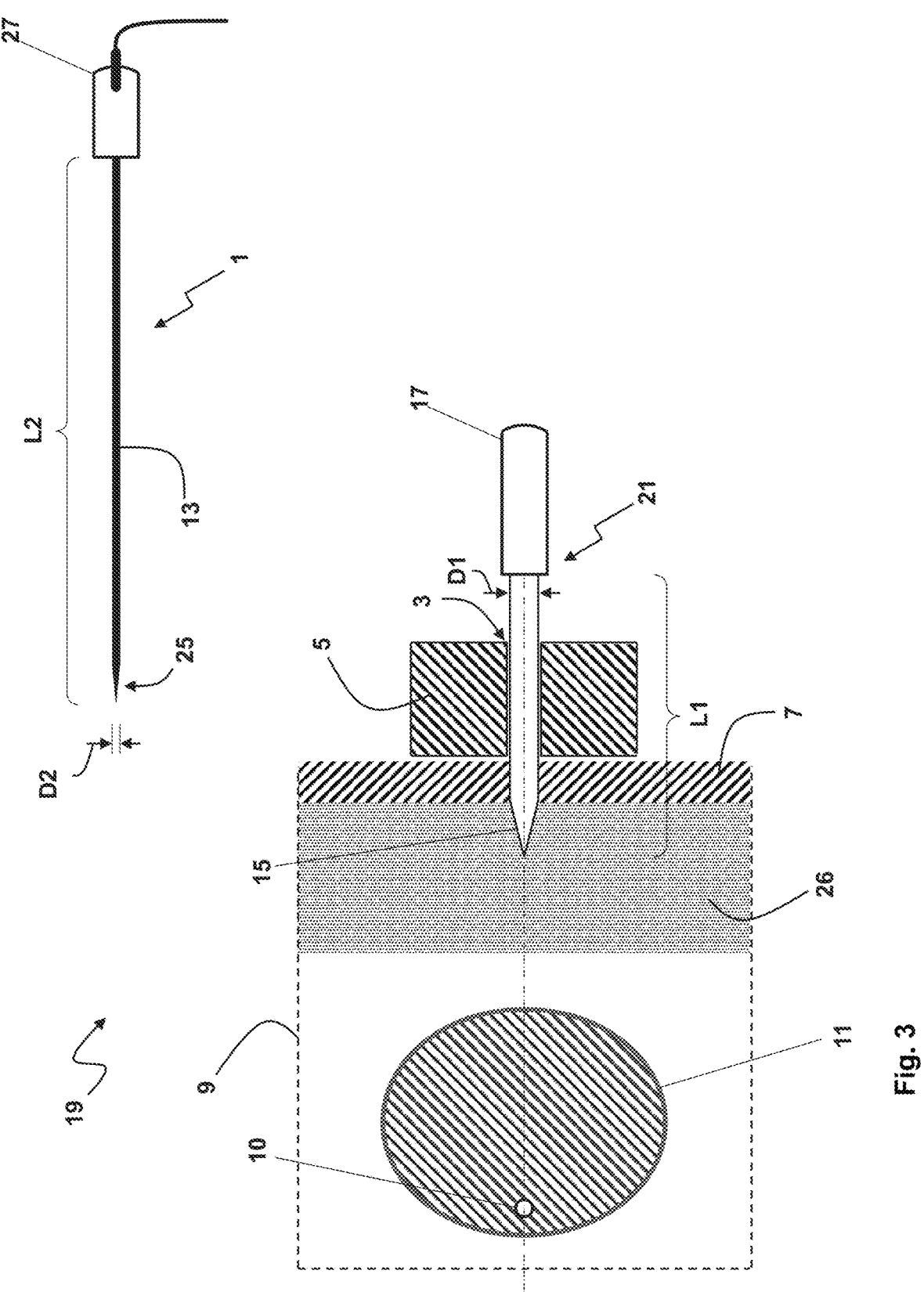
FIG. 3 and FIG. 4 are schematic longitudinal sectional views of an exemplary embodiment of the light applicator system disclosed herein at various stages during pre-piercing of the skin by means of a pre-piercing aid disclosed herein.
Figure 4:
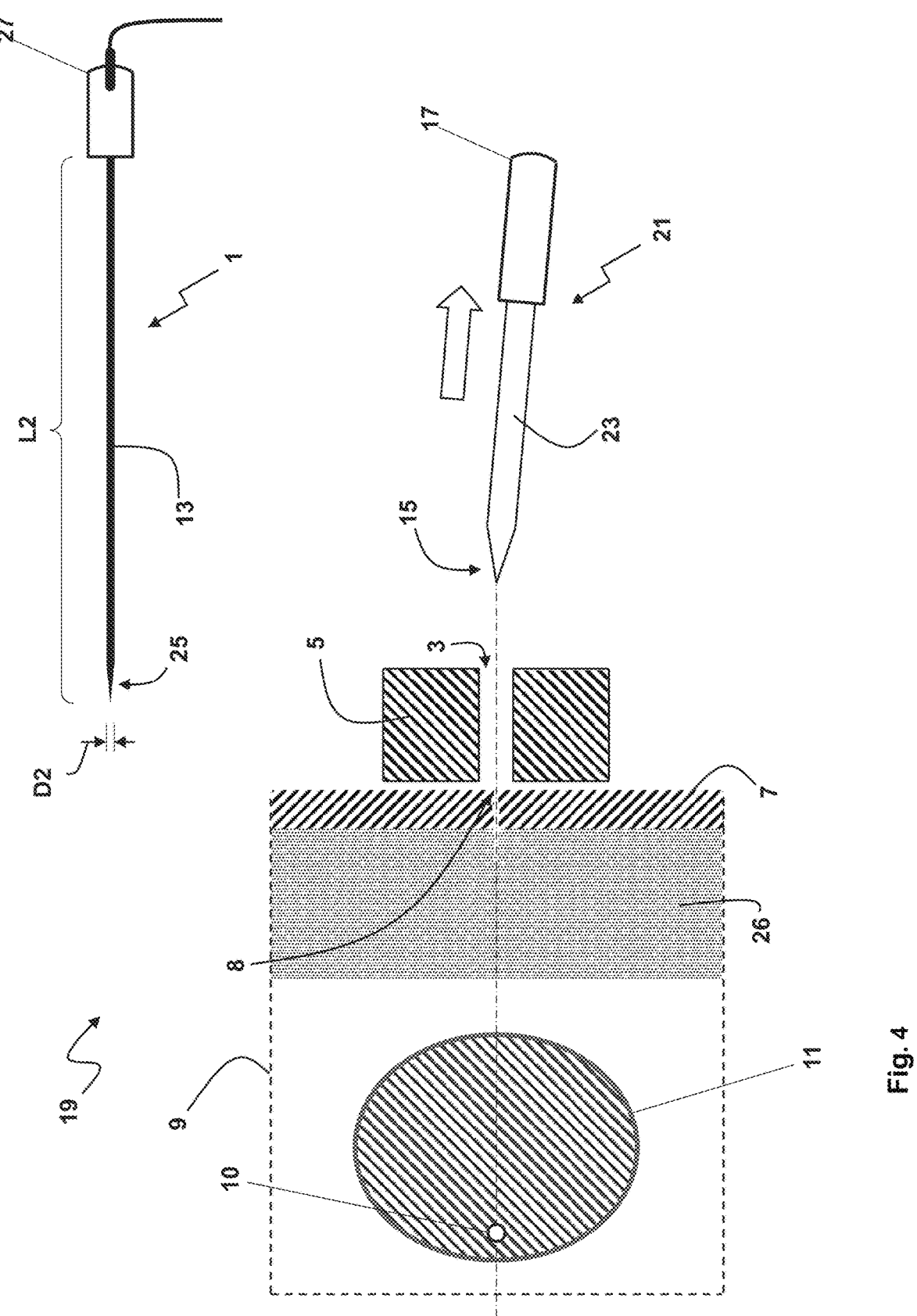

FIGS. 2 to 4 show a light applicator system 19 that solves this problem without making the insertion portion 13 of the light applicator 1 thicker and thus less minimally invasive. In this regard, the light applicator system 19 comprises a pre-piercing aid 21, which in the embodiment shown is a separate component from the light applicator 1. Before the light applicator 1 is pierced through the receptacle 3 of the positioning element 5 into the skin 7 with its needle tip 25 arranged axially centrally with respect to the insertion portion 13, the skin 7 is first pre-pierced by means of the pre-piercing aid 21 in order to reduce the skin resistance. The pre-piercing aid 21 is substantially in the form of a needle with a metallic pre-piercing aid shaft 23, a needle tip 15 arranged at the distal end of the pre-piercing aid shaft 23 and axially centrally with respect to this pre-piercing aid shaft 23, and a handle element 17 arranged at the proximal end of the pre-piercing aid shaft 23, wherein the pre-piercing aid shaft 23 has a substantially smaller length-to-diameter ratio than the insertion portion 13 of the light applicator 1, i.e. $L1/D1 \ll L2/D2$ and thus is substantially more flexurally rigid. Preferably, the pre-piercing aid shaft 23 has a length L1 which is substantially shorter than the length L2 of the insertion portion 13 of the light applicator 1 and/or a thickness D1 which is substantially thicker than the thickness D2 of the insertion portion 13 of the light applicator 1. The inner diameter of the receptacle 3 of the positioning element 5 corresponds here exactly to the outer diameter D1 of the pre-piercing aid shaft 23. The very rigid pre-piercing aid 21 is axially guided by the receptacle 3 of the positioning element 5 and, moreover, the needle tip 15 of the pre-piercing aid 21 is arranged axially centrally, so that a position 8 of the pre-piercing, i.e. the position of the opening 8 in the skin 7 created by the needle tip 15, which is to be found later by the needle tip 25 of the light applicator 1 by advancing same within the receptacle 3, is very precisely defined. The pre-piercing aid 21 can optionally be designed in such a way that it abuts with a stop, not shown here, at the axial position shown in FIG. 3, in which the pre-piercing aid 21 has stretched the skin 7 to the maximum. This protects the tissue 26 under the skin 7 from an unnecessarily deep pre-piercing with the relatively thick pre-piercing aid 21. FIG. 4 shows how the pre-piercing aid 21 is pulled out of the receptacle 3 of the positioning element 5 proximalwards after the pre-piercing and leaves a pre-pierced skin 7 at the precisely defined position 8, i.e. due to the required minimal invasiveness only a small opening, which later, when the light applicator 1 is introduced into the organic body 9, is nevertheless hit precisely by the needle tip 25 of the light applicator 1. It is important that the positioning element 5 remains fixedly positioned with respect to the skin 7, for example, that it remains glued on.

Figure 5C:
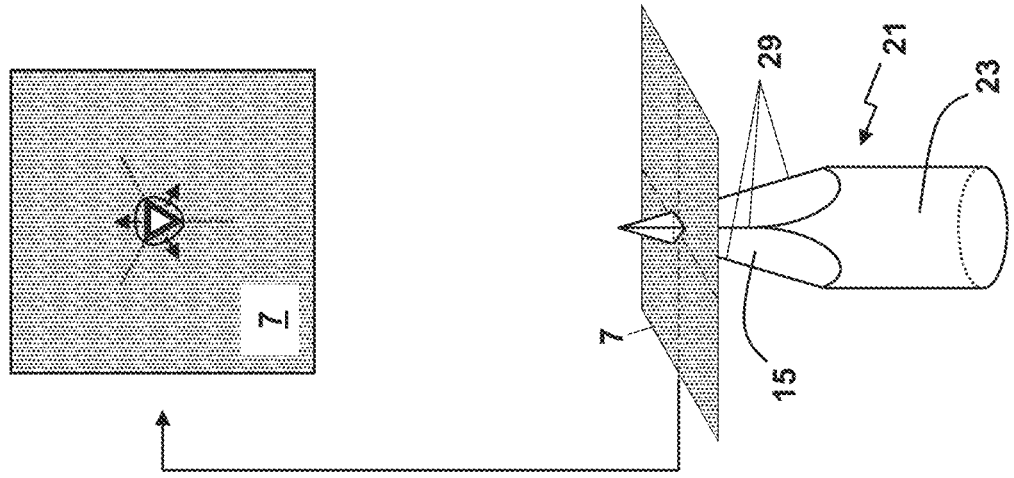
FIG. 5a, FIG. 5b, and FIG. 5c are schematic longitudinal sectional views of various embodiments of the needle tip of the pre-piercing aid disclosed herein.
Figure 5B:
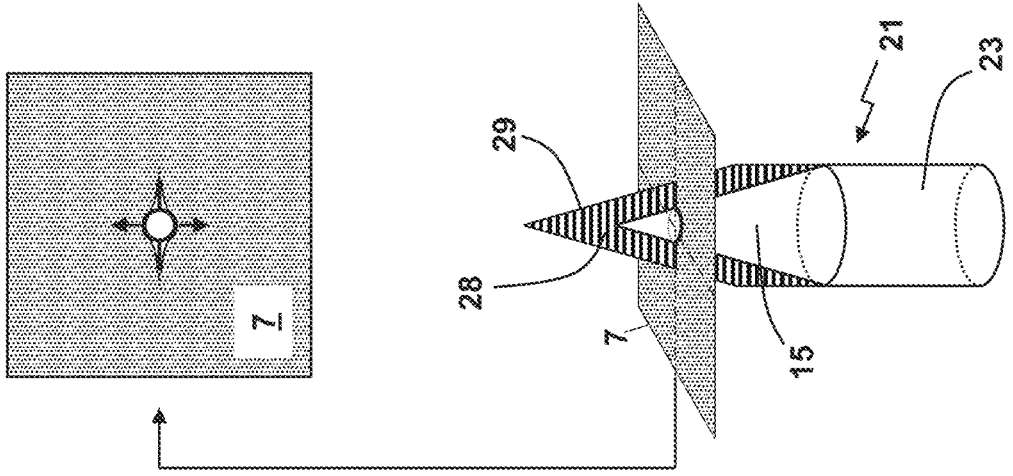
Figure 5A:
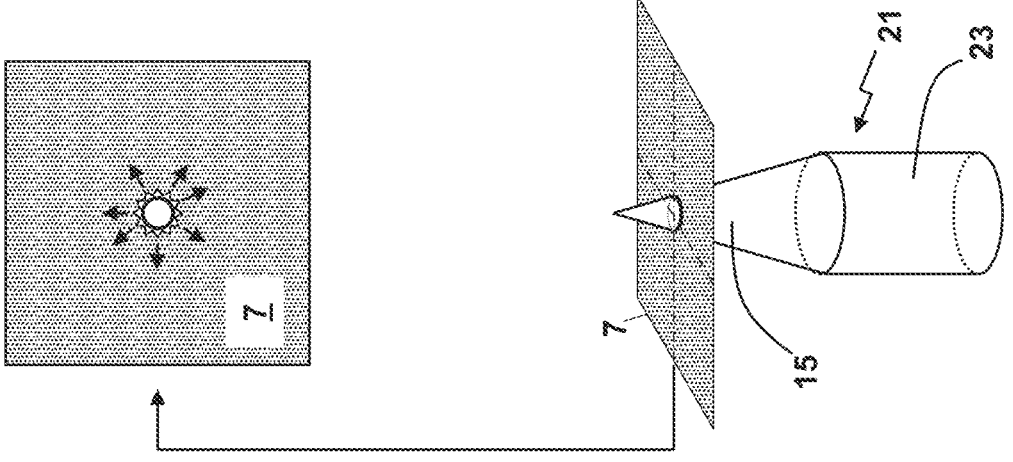

FIGS. 5a-c show various embodiments of the needle tip 15 of the pre-piercing aid 21. In FIG. 5a, the needle tip 15 is conical in the simplest form, so that the skin 7 is expanded with distal advancement. In order to reduce the resistance resulting from the stretching of the skin 7, the needle tip 15 in FIG. 5b has a cutting blade 28 which projects distally and forms a cutting edge 29 which cuts into the skin 7. This creates less skin tension so that the resistance of the skin 7 is reduced. In FIG. 5c it is shown that there can be multiple cutting edges 29 that do not have to protrude distally. In FIG. 5c, the needle tip 23 is pyramid-shaped, wherein the pyramid edges form the (here three) cutting edges 29.

Figure 6:
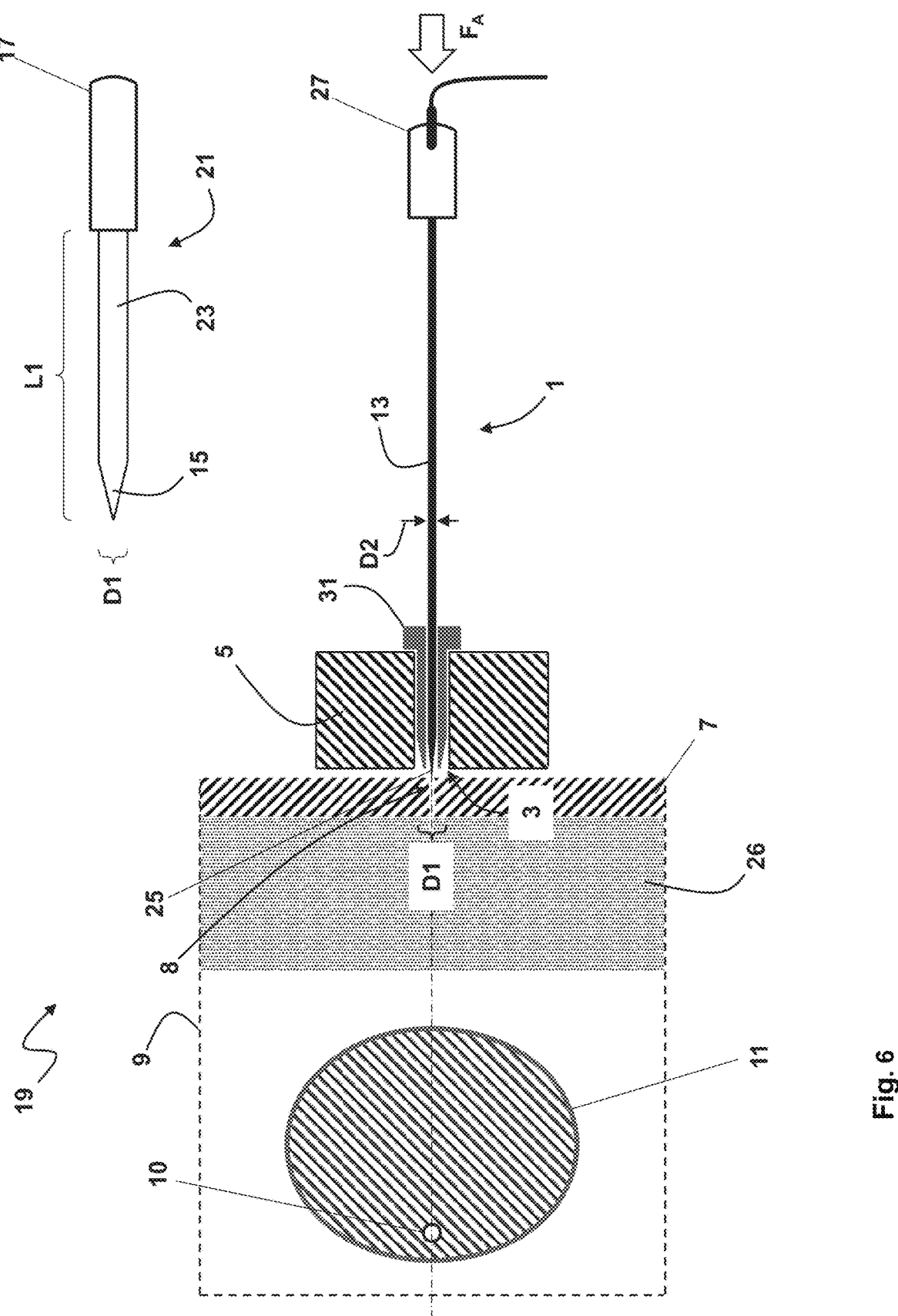
FIG. 6, FIG. 6a, FIG. 7, FIG. 8, FIG. 9, FIG. 10 and FIG. 11 are schematic longitudinal sectional views of various embodiments of the light applicator system disclosed herein.

FIG. 6 shows how the light applicator 1 can be used after the pre-piercing by means of the pre-piercing aid 21 now removed from the positioning element 5. Since the insertion portion 13 of the light applicator 1 is considerably thinner than the pre-piercing aid 21, an adapter sleeve 31 is provided which compensates for the difference between the thickness D1 of the pre-piercing aid shaft 23 and the thickness D2 of the insertion portion 13 of the light applicator 1, so that the inner diameter of the adapter sleeve 31 corresponds in a precisely fitting manner to the outer diameter D2 of the insertion portion 13 of the light applicator 1 and the adapter sleeve 31 has, at least in portions, an outer diameter D1 which fits precisely into a corresponding inner diameter of the receptacle 3 of the positioning element 5.

The adapter sleeve 31 can serve as a protective sleeve for the sensitive needle tip 25 of the light applicator 1 and can be captively pre-installed in an axially movable manner on the insertion portion 13 of the light applicator 1. Alternatively, the adapter sleeve 31 can first be manually inserted into the receptacle 3 and then the insertion portion 13 of the light applicator 1 can be inserted, or the adapter sleeve 31 can first be fitted onto the insertion portion 13 of the light applicator 1 and then inserted into the receptacle 3 together with the latter. The adapter sleeve 31 can also serve as a stabilising sleeve for the insertion portion 13 of the light applicator 1 in order to prevent, at least in portions, a bending of the insertion portion 13 of the light applicator 1 as shown in FIG. 1.

However, due to the pre-piercing of the skin 7 or the opening 8 thereby created by means of the pre-piercing aid 21 or its axially centrally arranged needle tip 15, the resistance of the skin 7 is already reduced to such an extent that the operator only has to exert a small manual force FA on the light applicator 1 in order to pierce the insertion portion 13 of the light applicator 1 into the body 9. Therefore, the risk of bending is already greatly reduced. The positioning element 5 as well as the equally axially central arrangement of the needle tip 25 of the light applicator 1 ensure here that the needle tip 25 of the light applicator 1, when advancing same within the receptacle 3, precisely hits the skin point 8 pre-pierced by means of the pre-piercing aid 21 or the skin point 8 pre-pierced by means of its axially centrally arranged needle tip 15, in order to thus reduce the resistance acting on the light applicator 1 by the skin. In order to provide sufficiently precise axial guidance so that, on the one hand, the defined skin point 8 is reached equally precisely by both needle tips 15 and 25 and, on the other hand, the relatively deep target tissue 11 is hit precisely with the needle tip 15 of the light applicator 1, the positioning element 5 preferably has a certain thickness in the axial direction of the receptacle 3. This means that the receptacle 3 has a sufficient length to achieve good guidance accuracy.

Figure 6A:
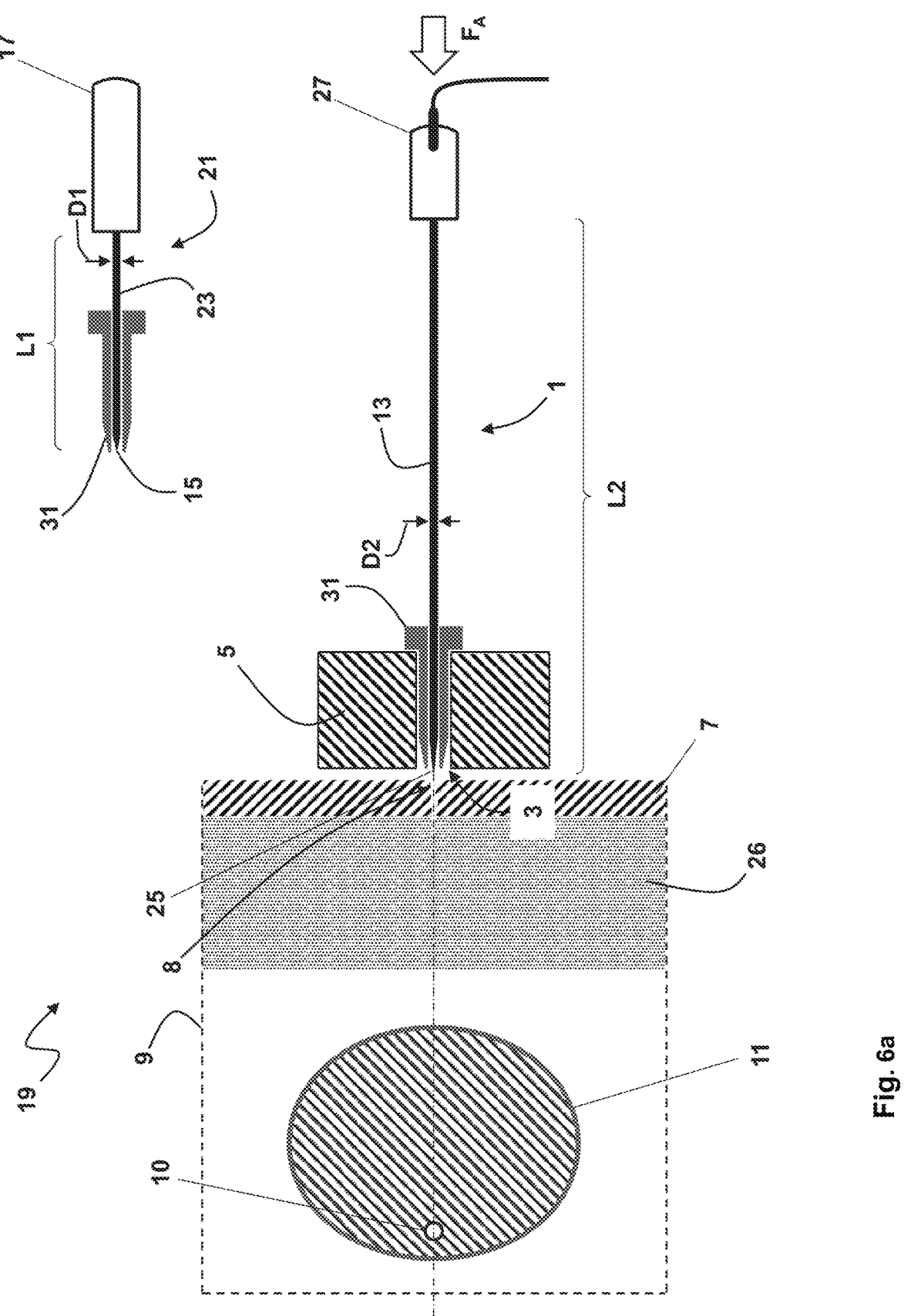

FIG. 6a shows a light applicator system 19 in which both the needle tip 25 of the light applicator 1 and the needle tip 15 of the pre-piercing aid 21 are each placed in their own adapter sleeve 31, which serves, among other things, to protect the operator, the positioning element 5 and the respective needle tip 15 or 25 itself, namely until it leaves the receptacle 3 of the positioning element on the distal side. For this purpose, the adapter sleeve 31 can already be attached in advance in a captive and axially movable manner to the pre-piercing aid shaft 23 or to the insertion portion 13 of the light applicator 1, wherein the respective needle tip 15 or 25 can preferably only move out of its adapter sleeve 31 when the adapter sleeve 31 has reached its final position in the receptacle 3 of the positioning element 5. In the present exemplary embodiment, the diameter D1 of the pre-piercing aid shaft 23 and the diameter D2 of the insertion portion 13 of the light applicator 1 are of the same size, so that the adapter sleeve 31 for the light applicator 1 and the adapter sleeve 31 for the pre-piercing aid 21 can be of identical construction. The inner diameter of the adapter sleeve 31 is adapted to the outer diameter D1 or D2 of the pre-piercing aid shaft 23 or of the insertion portion 13, and the outer diameter of the adapter sleeve 31 corresponds, at least in portions, to the inner diameter of the receptacle 3 of the positioning element 5. Since, firstly, the adapter sleeve 31 is of the same size with regard to its geometry (diameter) in the positioning element 5, the adapter sleeve 31 can be used for the pre-piercing aid shaft 23 or the insertion portion 13. Since, firstly, the adapter sleeve 31 is adapted to the insertion portion 13 of the light applicator 1, the pre-piercing aid shaft 23 and the receptacle 3 in terms of its geometry (diameter) in the manner described above, and since, in addition, both the needle tip 25 of the light applicator 1 is arranged centrally with respect to the axis of the insertion portion 13 of the light applicator 1 and the needle tip 15 of the pre-piercing aid 21 is arranged centrally with respect to the axis of the pre-piercing aid shaft 23, it is ensured that the needle tip 25 of the light applicator 1, after insertion and advancement into the receptacle 3 with its previously applied adapter sleeve 31, automatically or by itself finds the opening 8 already created in the skin 7 by the needle tip 15 of the pre-piercing aid 21, in order to thus significantly reduce the resistance caused by the tough skin 7, which the light applicator 1 experiences when it is inserted or advanced into or through the skin 7. In this exemplary embodiment, the increased flexural rigidity of the pre-piercing aid 21 compared to the light applicator 1 is achieved by making the pre-piercing aid shaft 23 significantly shorter than the insertion portion 13 of the light applicator 1, i.e.

L1<<L2. Here, too, the receptacle 3 has a sufficient length to achieve a good guiding accuracy of the light applicator 1 and the pre-piercing aid 21.

Another embodiment (without illustration) is based on the embodiment shown in FIG. 6a. However, the adapter sleeves 31 are not used for both the pre-piercing aid and the light applicator 1. However, in order to still achieve the desired guiding accuracy of the pre-piercing aid 21 and the light applicator 1 as a prerequisite for firstly both the pre-piercing aid 21 and the light applicator 1—in the sense of a reduction in resistance for the light applicator 1 on the skin 7—equally reaching the defined position of the opening 8 in the skin 7 and secondly the light applicator 1 then reaching the target point 10 in the organic body 9, now, in contrast to the embodiment of FIG. 6, the inner diameter of the receptacle 3 is adapted to the outer diameters D1 and D2 of the pre-piercing aid shaft 23 and the insertion portion 13 of the light applicator 1, which are the same size in this embodiment.

Figure 7:
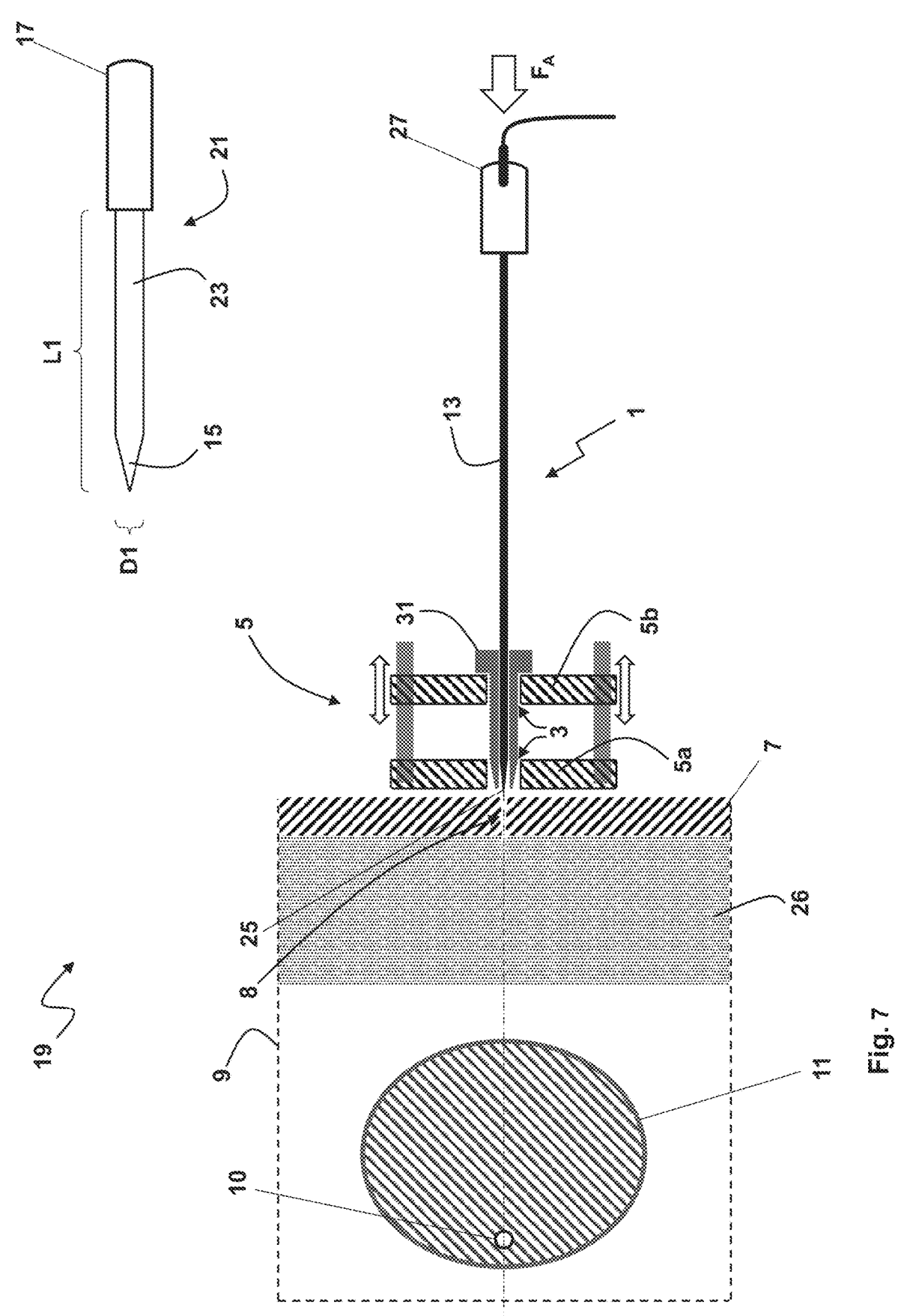

If the positioning element 5, for example as a perforated template, is several receptacles 3 for simultaneously receiving several light applicators 1, the embodiments shown in FIG. 6 and FIG. 6a have the disadvantage that the positioning element 5 is relatively bulky and possibly heavy. While this may be acceptable or even advantageous for certain applications, it is disadvantageous for most applications. In FIG. 7, an exemplary embodiment of the positioning element 5 is shown in which the positioning element 5 comprises two axially spaced positioning element components 5a, 5b, each having at least one receptacle 3 axially aligned with a corresponding receptacle 3 of the other component. Preferably, the axial distance between the positioning element components 5a, 5b is adjustable, as schematically shown in FIG. 7. The greater the distance, the better the guiding accuracy. A smaller distance may be useful for handling when positioning the positioning element 5 relative to the organic body 9. In contrast to the exemplary embodiments according to FIGS. 6 and 6a, a corresponding guiding accuracy can be achieved with less volume and weight of the positioning element 5.

Figure 8:
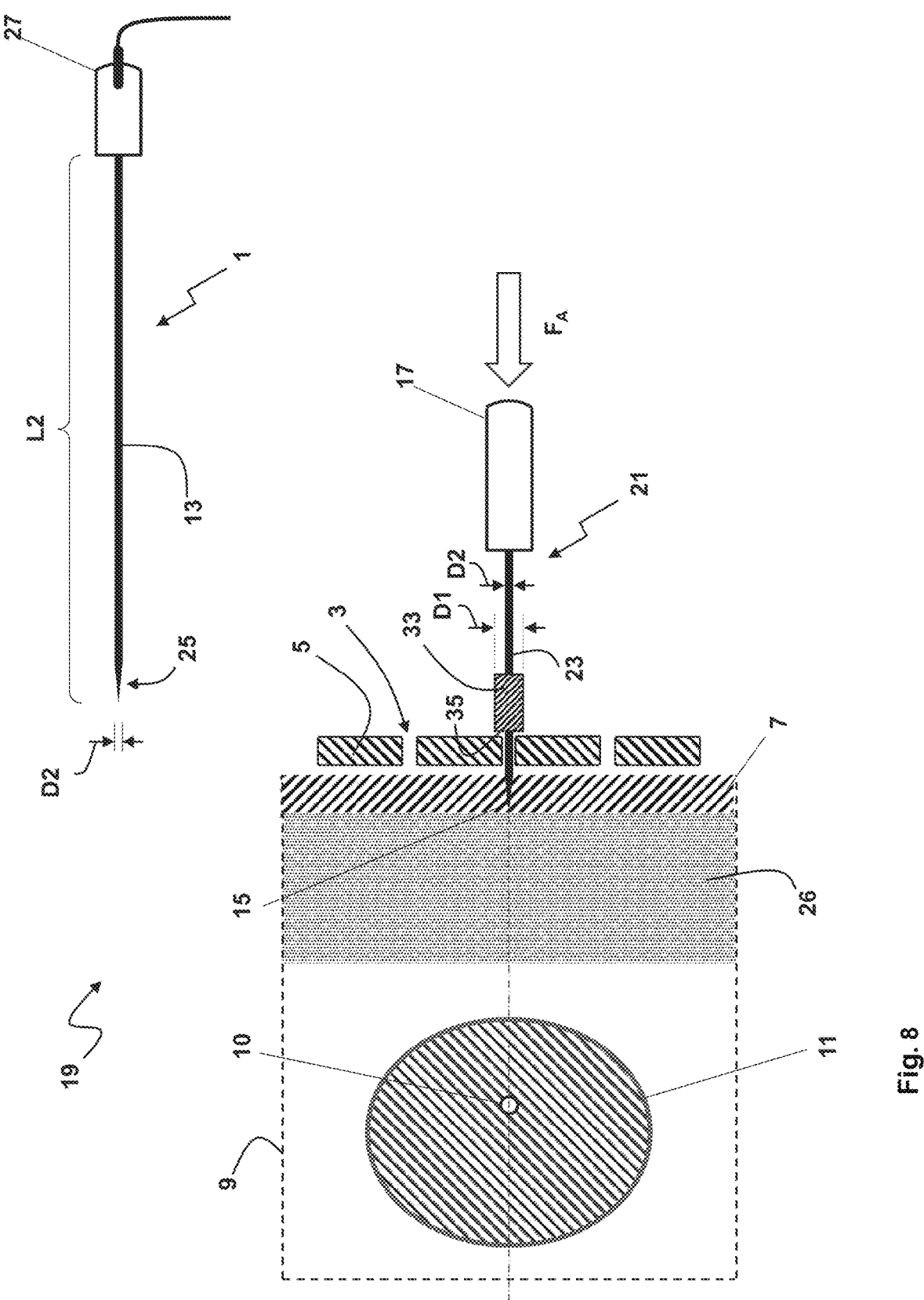

FIG. 8 shows an embodiment of the pre-piercing aid 21 in which the pre-piercing aid shaft 23 has a thickness D1 only in portions in a thickening portion 33, which is thicker than the thickness D2 of the insertion portion 13 of the light applicator 1 and thus a higher flexural rigidity is achieved for the pre-piercing of the skin 7. Distally of the thickening portion 33, the outer diameter of the pre-piercing aid shaft 23 corresponds to the thickness D2 of the insertion portion 13 of the light applicator 1. This has the advantage that the receptacle 3 in the positioning element 5 can be made thinner with an inner diameter D2, so that more receptacles 3 per unit area can be accommodated in the positioning element 5, which is advantageous for close-meshed positioning of several parallel light applicators 1. In addition, no adapter sleeve 31 is required for the light applicators 1. A distal end of the thickening portion 33 can abut against positioning element 5 as a stop 35 when a desired pre-piercing depth through the skin 7 is reached.

Figure 9:
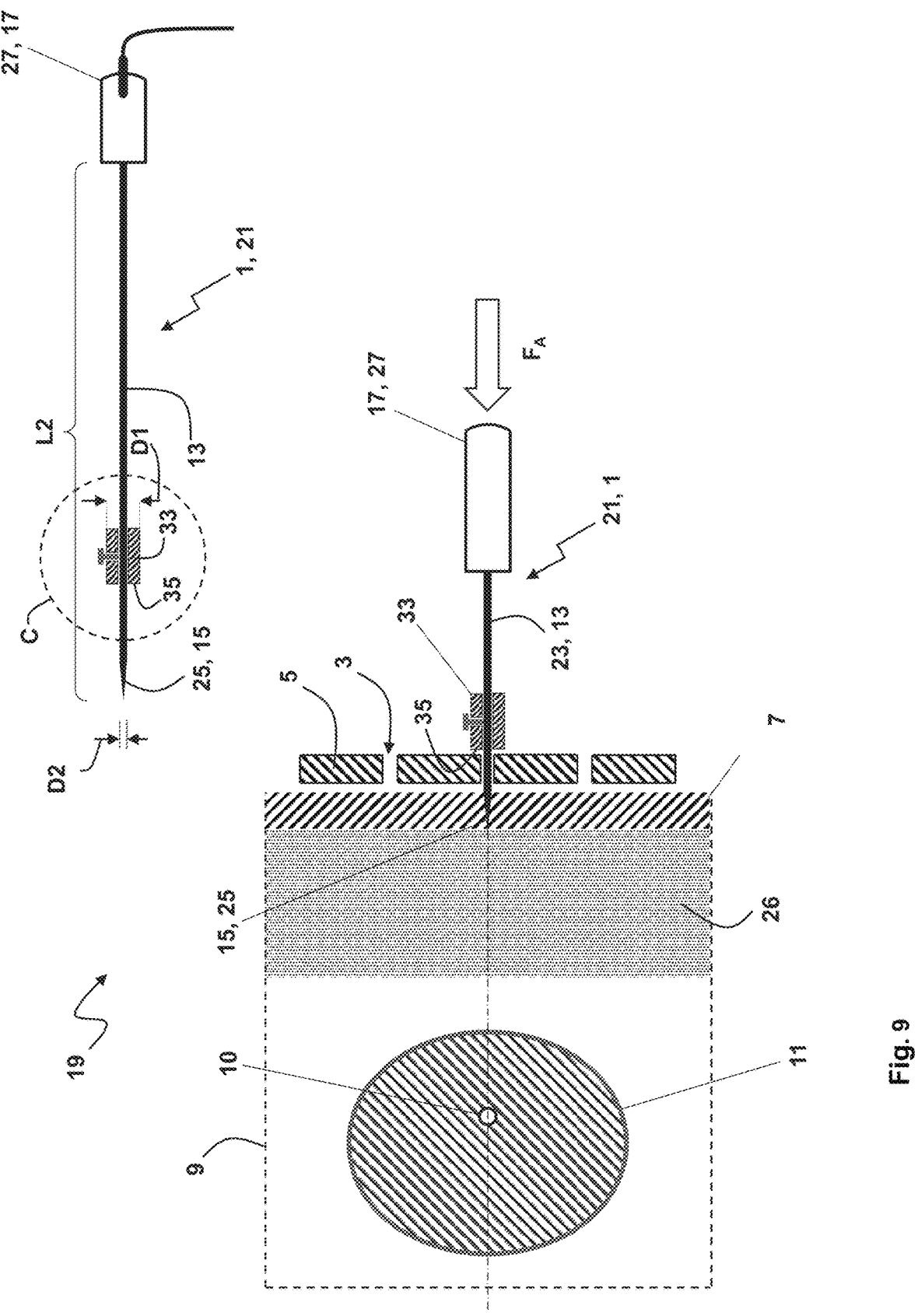

In FIG. 9, an optional embodiment of the invention is indicated by a dashed circle C, in which the pre-piercing aid 21 does not have to be a separate component, but can be integrated into the light applicator. The thickening portion 33 can, for example, be realised by a stabilising sleeve with an outer diameter D1 which can be axially positioned and fixed on the insertion portion 13 of the light applicator 1. In this case, the pre-piercing aid shaft 23 is formed by the insertion portion 13 of the light applicator 1, and the needle tip 25 of the light applicator 1 is the needle tip 15 of the pre-piercing aid 21. The stabilising sleeve 33 in this case locally increases the flexural rigidity of the insertion portion 13 of the light applicator 1, so that it does not bend or bends only insignificantly when pre-piercing into the skin. The stabilising sleeve 33 can be fixed, for example, by means of a clamping screw or jaw at a selected axial position on the pre-piercing aid shaft 23, in order to adjust the stop position 35 and thus the pre-piercing depth and to adapt it to the application. The pre-piercing aid 21 can of course be designed as a separate component as an alternative to an embodiment integrated into the light applicator 1 as described above, and can preferably be considerably shorter than the light applicator 1.

Figure 10:
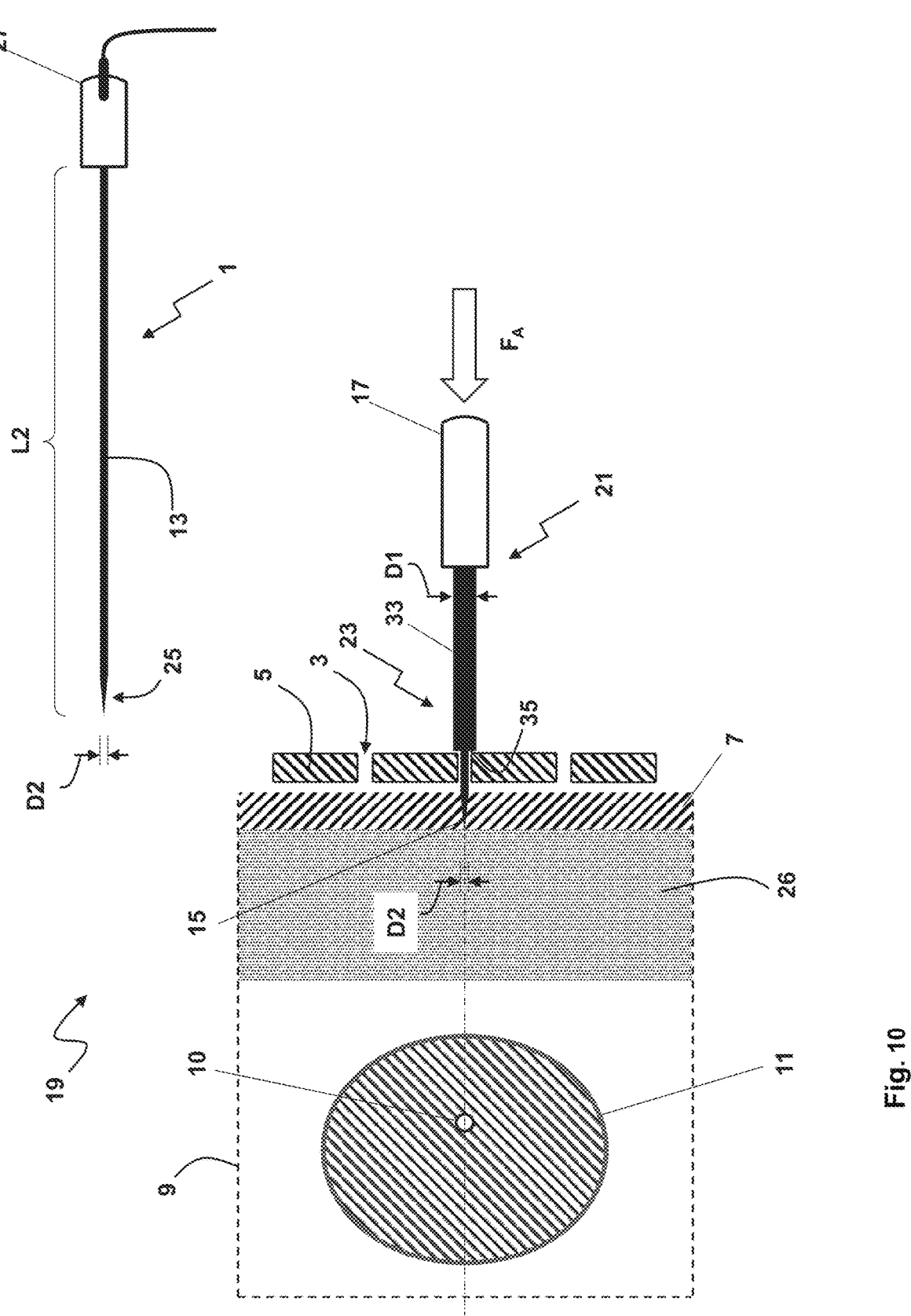
Figure 11:
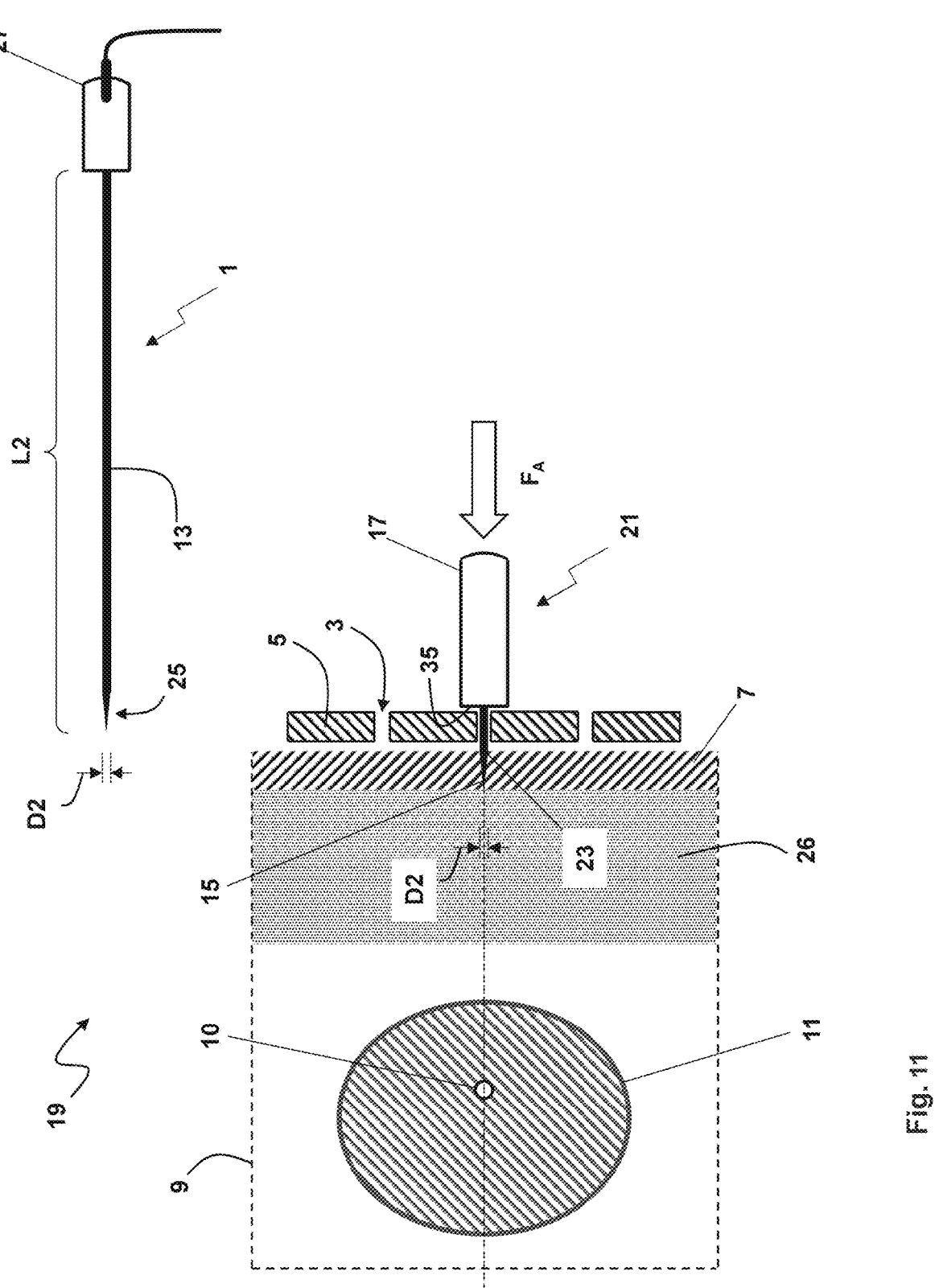

FIGS. 10 and 11 show different embodiments for the realisation of the stop 35. In FIGS. 8 and 9, a distal end of the thickening portion 33 forms the stop 35, which abuts against the positioning element 5 when a desired or set pre-piercing depth through the skin 7 is reached. In FIG. 10, a distal portion of the pre-piercing aid shaft 23 has a thinner diameter D2 compared to a proximal portion of the pre-piercing aid shaft 23, which has a thicker diameter D1. The proximal portion of the pre-piercing aid shaft 23 thus functions as a thickening portion 33, the distal end of which forms the stop 35. This is advantageous for the flexural rigidity of the pre-piercing aid shaft 23. The exemplary embodiment according to FIG. 11 manages entirely without the proximal portion of the pre-piercing aid shaft 23, wherein the pre-piercing aid shaft 23 is so short that it consists only of the distal portion with the thin diameter D2. The stop 35 is formed here by the handle element 17. The shortness of the pre-piercing aid shaft 23 is advantageous for the flexural rigidity.

Figure 12:
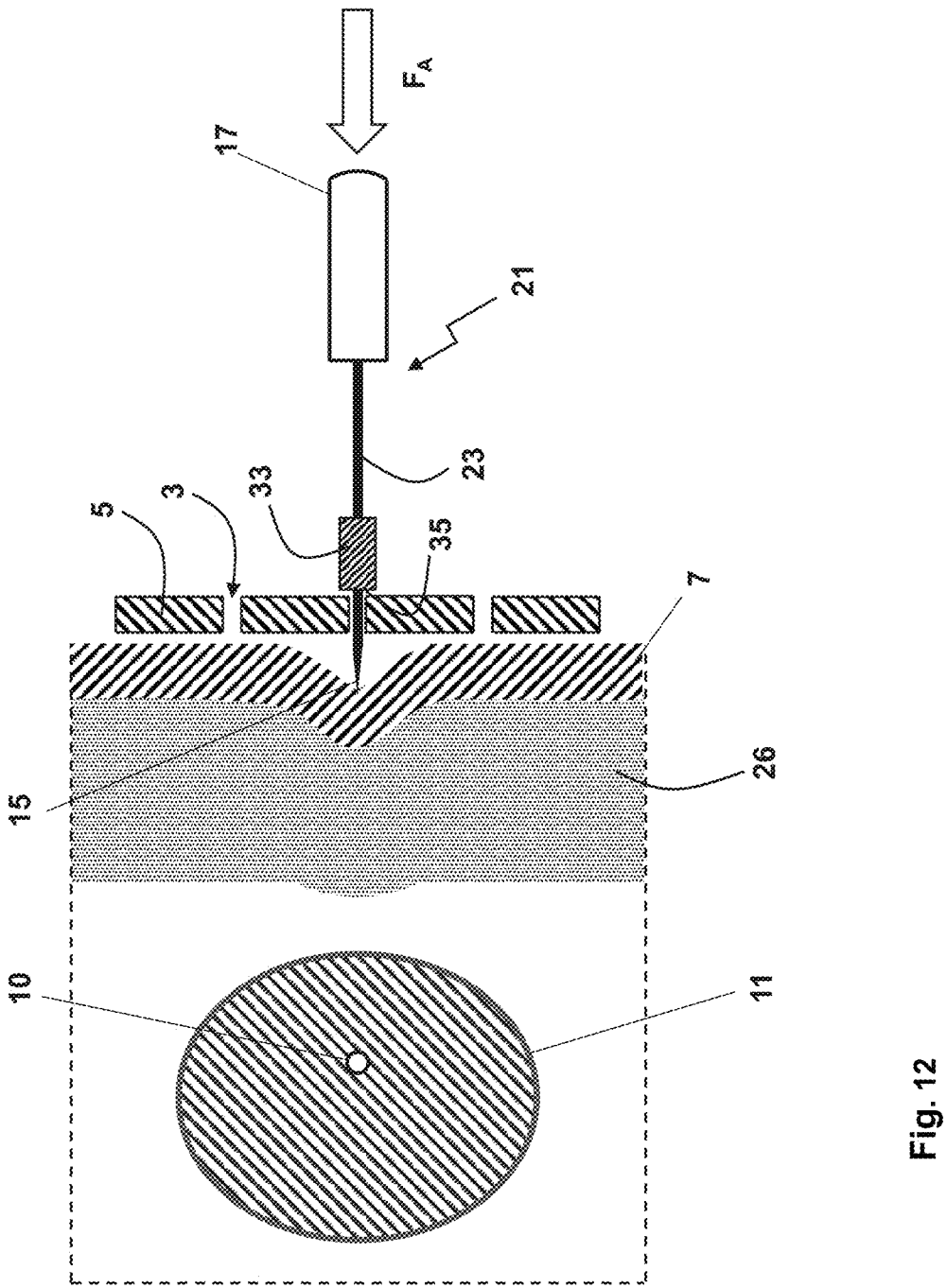
FIG. 12, FIG. 13 and FIG. 14 are schematic longitudinal sectional views of an embodiment of the light applicator system disclosed herein at various stages of the pre-piercing of the skin to illustrate the problem with highly yielding skin of the patient.
Figure 13:
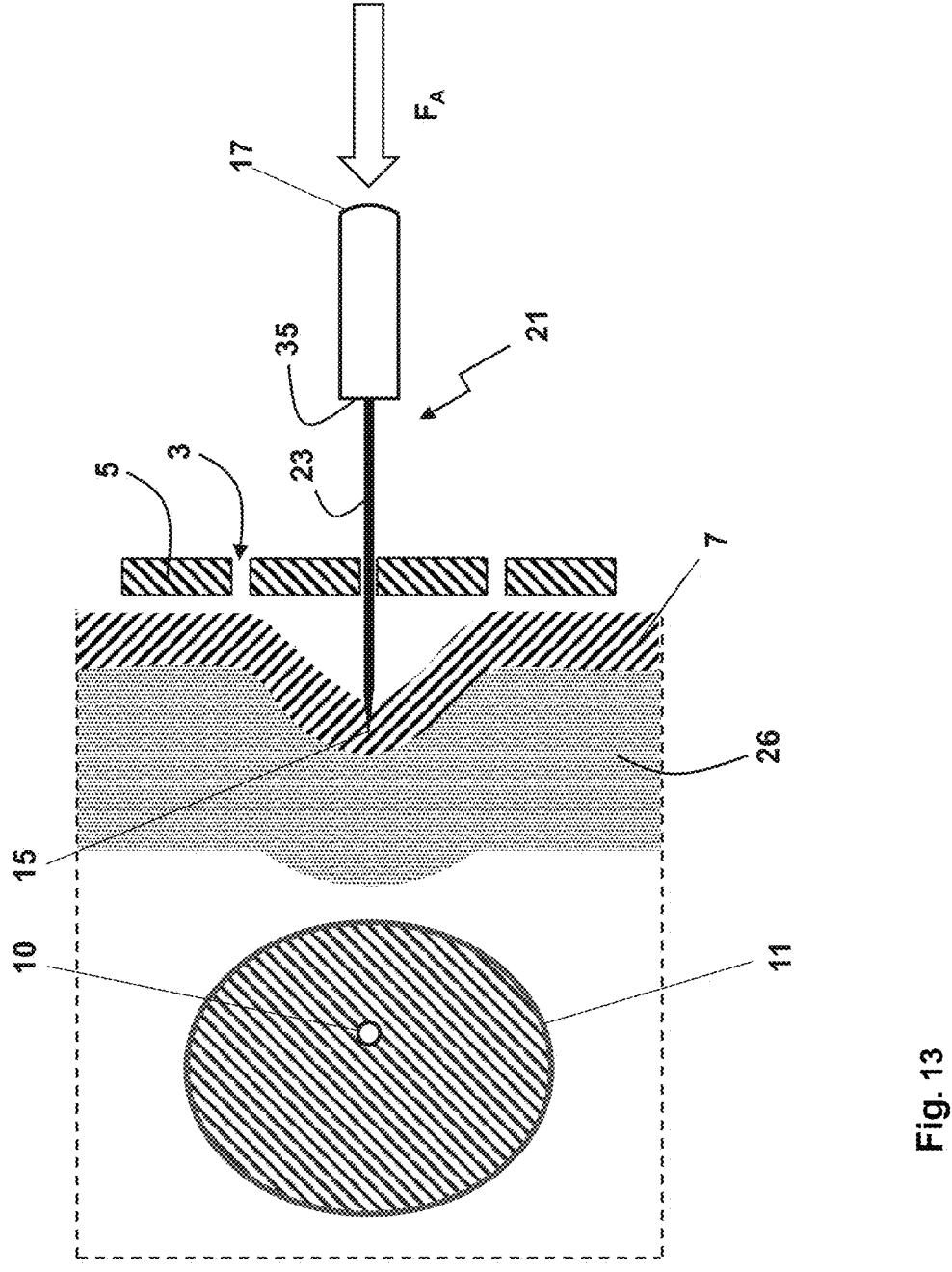
Figure 14:
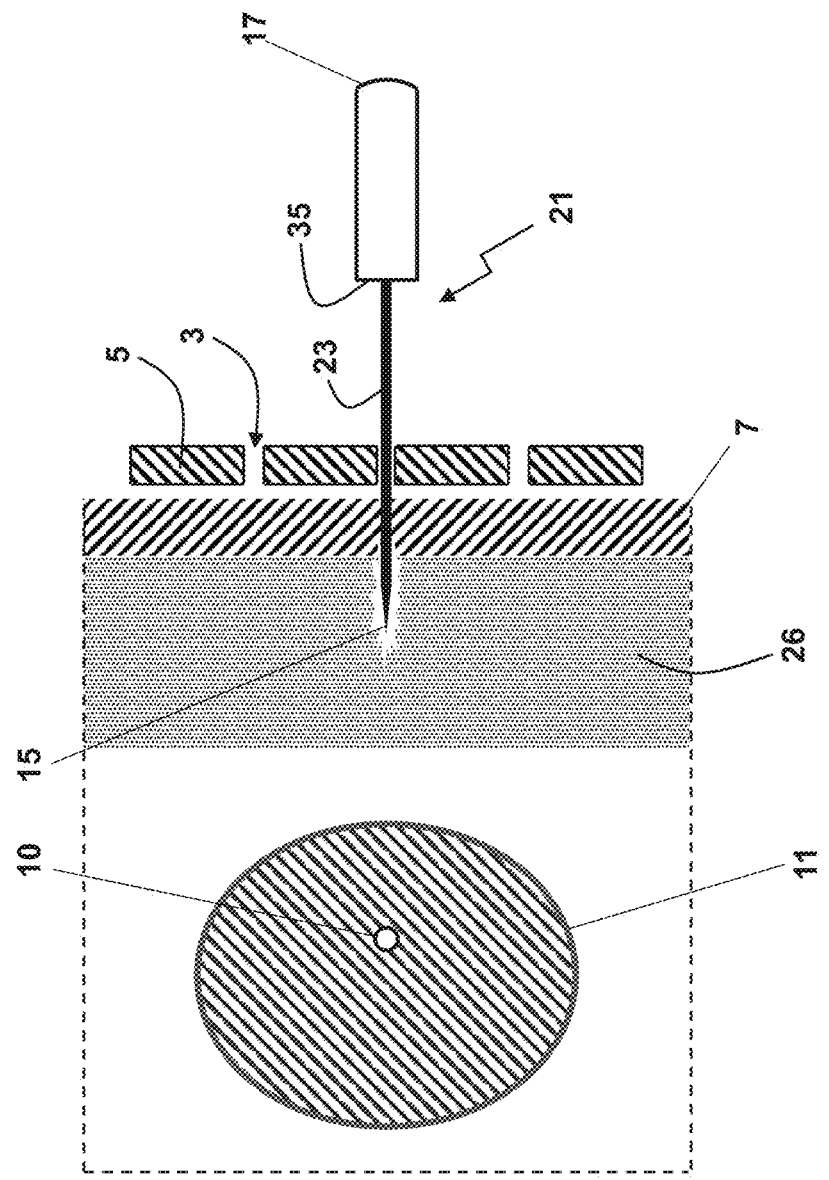

FIGS. 12 to 14 show a problem with particularly yielding and/or leathery skin 7. During the pre-piercing, the skin 7 may yield distalwards, as shown in FIG. 12. This risk is already reduced when the positioning element 5 is glued to the skin 7. However, even then the skin 7 may detach distalwards and dent instead of opening for the pre-piercing of the needle tip 15 of the pre-piercing aid 21. If this happens as far as the stop 35, as shown in FIG. 12, the pre-piercing has virtually no effect. Since the positioning element 5 blocks the view of the pre-piercing site, the operator may not notice the ineffectiveness of the pre-piercing. For this purpose, the positioning element 5 can preferably be made transparent at least around the receptacle 3, but due to reflections at optical interfaces, a view of the pre-piercing site may remain blocked.

As the skin 7 stretches during the (unsuccessful) pre-piercing, the reaction force of the skin 7 and the corresponding pressure exerted by the needle tip 15 on the skin 7 increases distalwards. If, as in FIG. 13, an attempt is made to increase the pre-piercing depth by moving the stop 35 proximally in order to achieve the reaction force of the skin 7 required for a successful pre-piercing, the undesirable situation shown in FIG. 14 may occur. The skin 7 opens abruptly at a certain pre-piercing depth and springs back proximally. Because of the greater pre-piercing depth, the needle tip 15 pierces tissue 26 under the skin 7 into which the pre-piercing aid 21 should not actually be pre-pierced. The pre-piercing is therefore less minimally invasive than desired.

Figure 15:
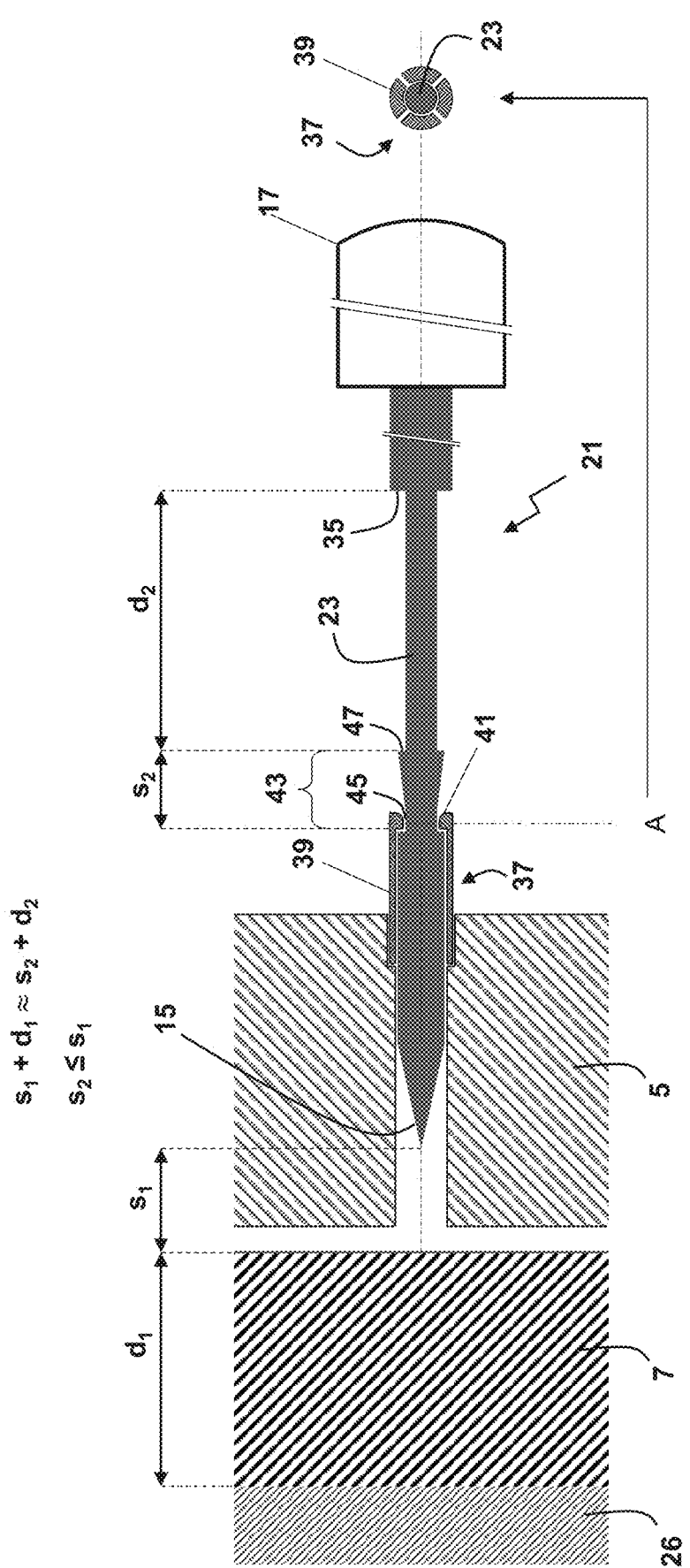
FIG. 15, FIG. 16, FIG. 17 and FIG. 18 are schematic longitudinal sectional views of an embodiment of the light applicator system disclosed herein at various stages when pre-piercing the skin to illustrate the solution to the problem when the patient's skin is highly yielding.

The exemplary embodiment shown in FIGS. 15 to 18 solves the problem of particularly yielding and/or leathery skin 7 shown in FIGS. 12 to 14. For this purpose, a resistance component 37 is provided to take over from the skin 7 the function of building up a reaction force in order to build up the pressure on the skin 7 necessary for the pre-piercing. The resistance component 37 is here a sleeve arranged on the positioning element 5 and axially slotted from the proximal side, which forms resiliently radially outwardly yielding spring legs 39 with radially inwardly extending feet 41. The pre-piercing aid shaft 23 has an axial portion 43, the outer diameter of which gradually and/or incrementally increases from a distal end 45 proximally to a maximum diameter at a proximal end 47 of the portion 43. Proximally of the proximal end 47 of the portion 43, the pre-piercing aid shaft 23 is again thinner. FIG. 15 shows an axial position at the start of the pre-piercing, with the spring legs 39 of the resistance component 37 in relaxed axial alignment and the feet 41 resting against the pre-piercing aid shaft 23 at the distal end 45 of the portion 43. The distal end of the needle tip 15 of the pre-piercing aid 21 still has an axial distance $s_1$ to the skin 7 here, which corresponds at least to the axial length $s_2$ of the portion 43.

Figure 16:
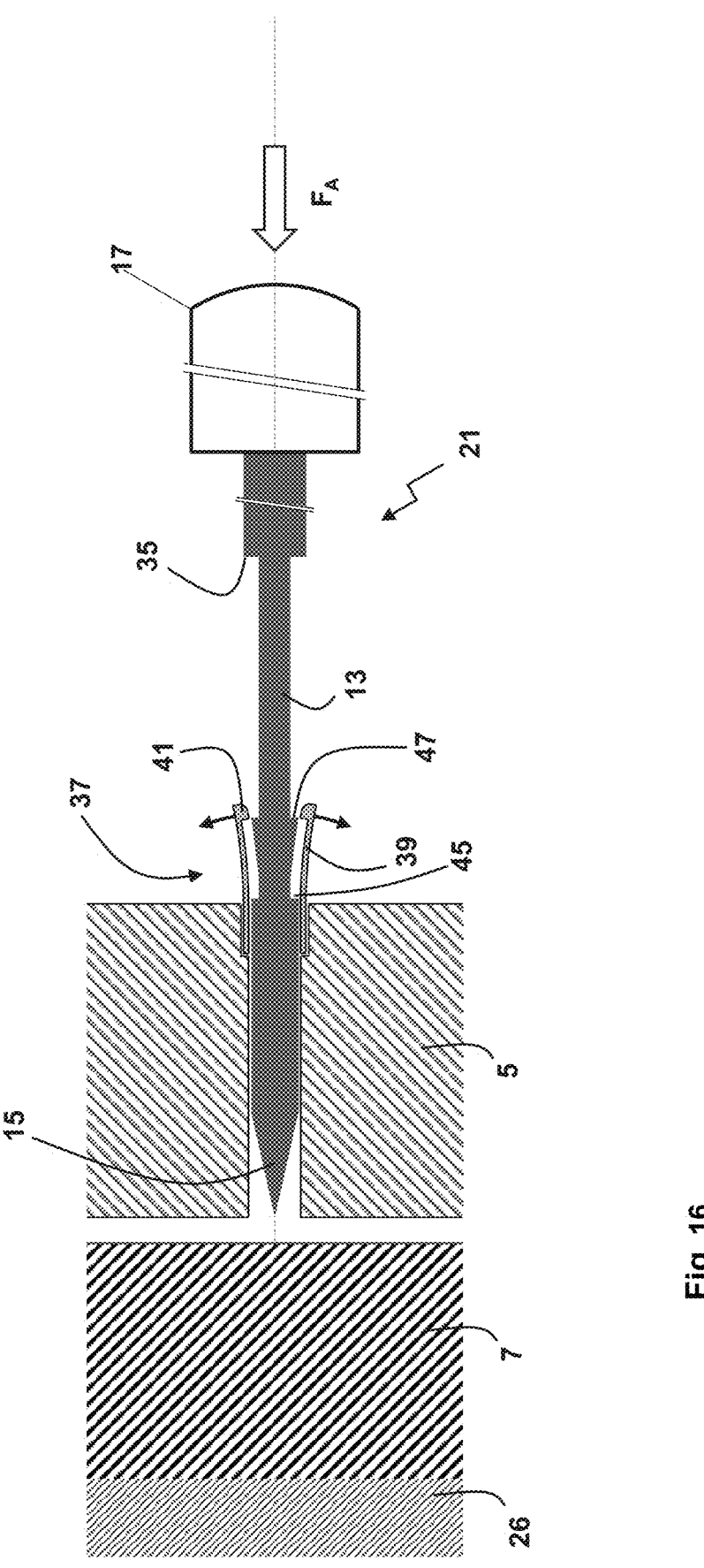

If the pre-piercing aid 21 is now pushed distally, as shown in FIG. 16, the spring legs 39 bend outwards against their radially inward restoring force, as the feet 41 are pressed radially outwards by the increasing diameter. For this, the operator must exert a distally directed manual force on the handle element 17. This is at a maximum with the maximum tension of the spring legs 39 shown in FIG. 16, when the feet 41 have reached the distal end 47 of the portion 43.

Figure 17:
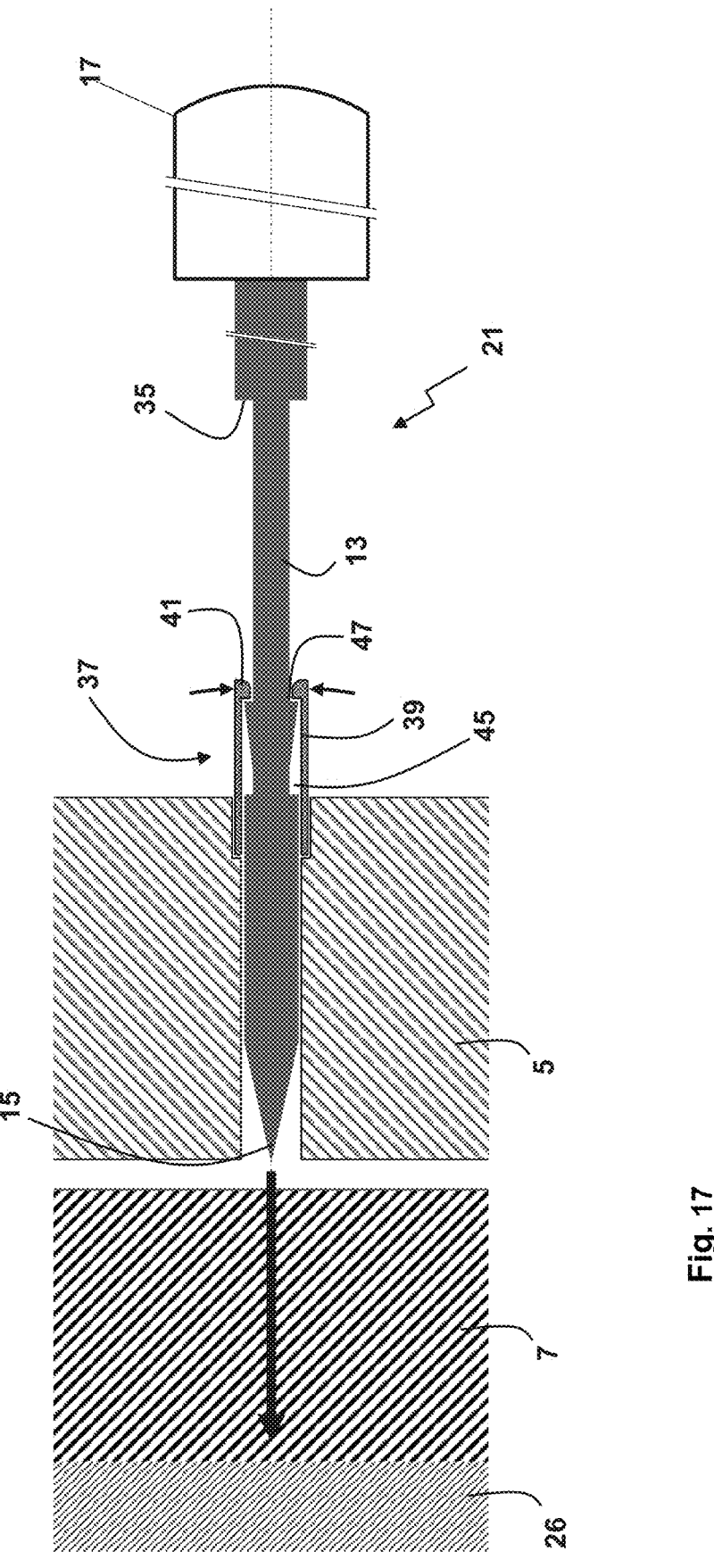
Figure 18:
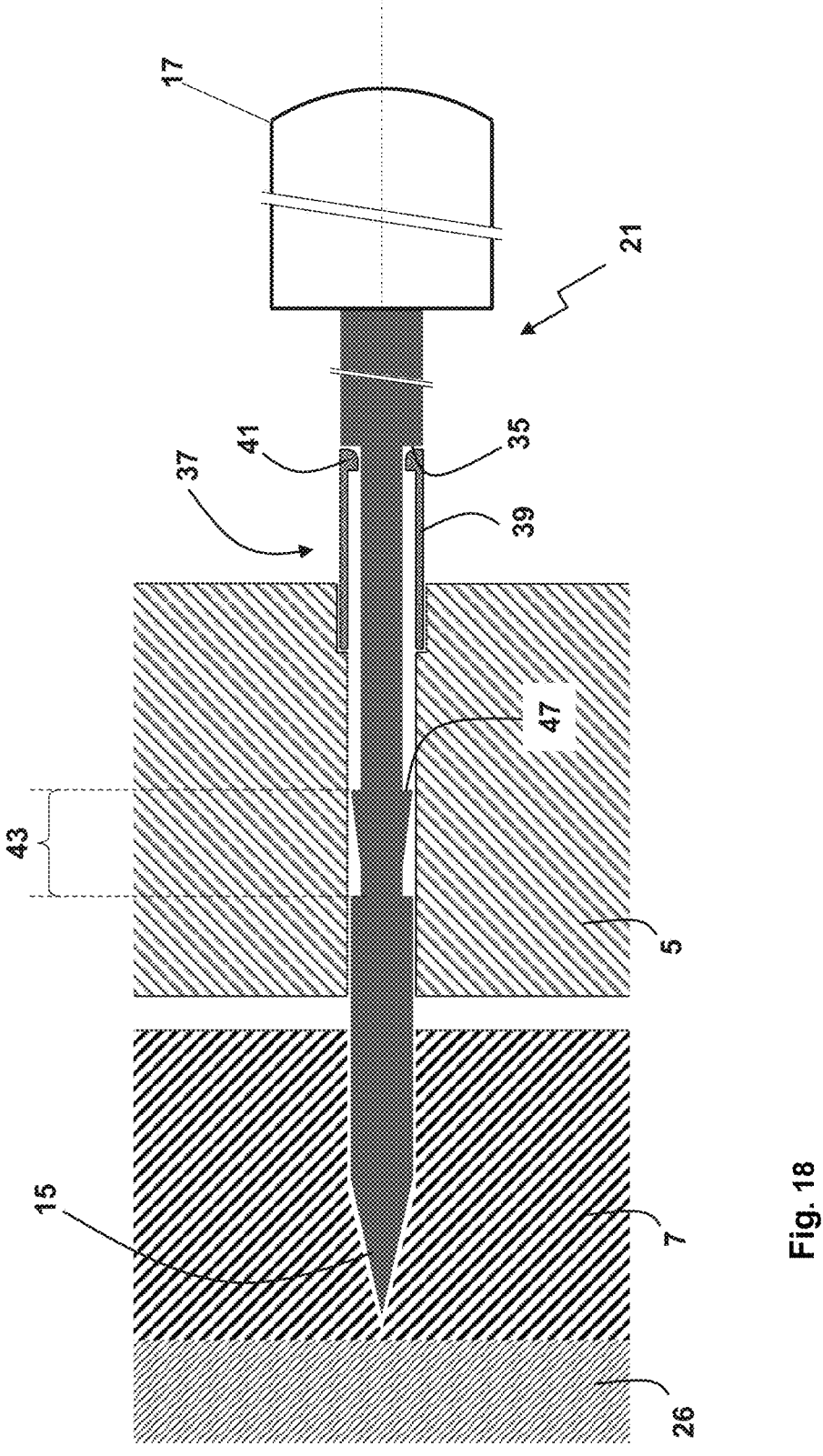

As soon as the pre-piercing aid 21 is pushed distalwards beyond the point shown in FIG. 16, the spring legs 39 snap back abruptly into their relaxed axial orientation, as shown in FIG. 17. The manual force of the operator still acting now leads to a force impact with corresponding distal acceleration of the pre-piercing aid 21. The needle tip 15 of the pre-piercing aid 21 thus hits, with this force impact, against the skin 7, which cannot yield so quickly due to its inertia and the pressure is immediately so great that the skin 7 opens for the pre-piercing, as shown in FIG. 18.

The pre-piercing aid shaft 23 forms a stop 35, proximally of the proximal end 47 of the portion 43, for the feet 41 of the spring legs 39, so that the pre-piercing aid 21 is stopped at the intended pre-piercing depth by the feet 41 hitting the stop 35. The distance $d_2$ of the stop 35 from the proximal end 47 of the portion 43 corresponds here approximately to the thickness $d_1$ of the skin 7, so that this is pierced completely, but the needle tip 15 is not pierced or is only very slightly pierced into the tissue 26 lying under the skin 7. If the needle tip 15 is to hit the skin 7 already at speed, i.e. $s_1>s_2$, then preferably correspondingly $d_2>d_1$ so that $s_1+d_1 \approx s_2+d_2$ applies.

The resistance component 37 can be part of or attached or attachable to the positioning element 5. Alternatively, the resistance component 37 can be part of the pre-piercing aid 21 and/or attached or attachable thereto. Preferably, it can be captively attached to the pre-piercing aid shaft 23 as an axially movable sleeve.

The numbered designations of the components or directions of movement as "first", "second", "third", etc. are chosen herein purely arbitrarily to distinguish the components or directions of movement from one another and can be chosen arbitrarily differently. This does not imply any order of importance. A designation of a component or technical feature as "first" should not be misunderstood to mean that there must be a second component or technical feature of this type. Furthermore, any method steps can be carried out in any order and/or partially or completely overlapping in time, unless explicitly explained otherwise or imperatively required.

Equivalent embodiments of the parameters, components or functions described herein that would appear obvious to a person skilled in the art in light of this description are intended to be included herein as if they had been explicitly described. Accordingly, the scope of the claims is intended to encompass such equivalent embodiments. Any "can" features designated as optional, advantageous, preferred, desirable or similar are to be understood as optional and not as limiting the scope of protection.

The described embodiments are to be understood as illustrative examples and do not constitute an exhaustive list of possible embodiments. Any feature disclosed in the context of an embodiment may be used alone or in combination with one or more other features, regardless of the embodiment in which the features were described in each case. While at least one exemplary embodiment is described and shown herein, variations and alternative embodiments that would appear obvious to a person skilled in the art in view of this description are included within the scope of protection of this disclosure. Moreover, the term "have" herein is not intended to exclude additional other features or process steps, nor is "one" or "a" intended to exclude a plurality.

While specific embodiments of the invention have been shown and described in detail to illustrate the application of the principles of the invention, it will be understood that the invention may be embodied otherwise without departing from such principles.

LIST OF REFERENCE CHARACTERS

1 light applicator
3 receptacle
5 positioning element
7 skin
8 position of the pre-piercing, opening in the skin, pre-pierced skin point
9 organic body
10 target point
11 target tissue
13 insertion portion
15 needle tip of the pre-piercing aid
17 handle element of the pre-piercing aid
19 light applicator system
21 pre-piercing aid
23 pre-piercing aid shaft
25 needle tip of the light applicator
26 tissue lying under the skin
27 handle element of the light applicator
28 cutting blade
29 cutting edge(s)
31 adapter sleeve
33 thickening portion/stabilising sleeve
35 stop
37 resistance component
39 spring legs
41 feet
43 portion of the pre-piercing aid shaft
45 distal end of the portion of the pre-piercing aid shaft
47 proximal end of the portion of the pre-piercing aid shaft
D1 diameter of the pre-piercing aid shaft
L1 length of the pre-piercing aid shaft
D2 diameter of the insertion portion of the light applicator
L2 length of the insertion portion of the light applicator
$d_1$ thickness of the skin $s_1$ distance of the needle tip of the pre-piercing aid to the skin $d_2$ distance of the stop from the proximal end of the portion 43

$s_2$ axial length of the portion 43

The invention claimed is:

1. A light applicator system for examination and/or treatment of an organic body, the light applicator system comprising:

at least one light applicator;

a positioning element, wherein the light applicator has a distal-side insertion portion with at least one actively light-emitting element and a needle tip arranged axially centrally with respect to the insertion portion at the distal end for piercing tissue of the organic body, wherein the positioning element is fixable at least temporarily in a defined position and orientation relative to the organic body and has at least one receptacle for the at least one light applicator, in which the at least one light applicator has, at least temporarily, a defined position and orientation relative to the organic body and in which the needle tip of the light applicator is guided axially centred with respect to the at least one receptacle of the positioning element; and a pre-piercing aid with a pre-piercing aid shaft and a distal needle tip arranged axially centrally with respect to the pre-piercing aid shaft, wherein the pre-piercing aid also fits into the at least one receptacle of the positioning element in such a way that the needle tip of the pre-piercing aid is guided axially centred in said receptacle with respect to the at least one receptacle of the positioning element, and that the pre-piercing aid has, at least temporarily, a defined orientation relative to the organic body which corresponds to the defined orientation relative to the organic body of the at least one light applicator.

2. The light applicator system according to claim 1, wherein the pre-piercing aid is a component separate from the light applicator which, after a pre-piercing into the organic body, can be removed from the at least one receptacle of the positioning element in order to subsequently introduce the light applicator through the at least one receptacle of the positioning element into the pre-pierced organic body for examination and/or treatment of the organic body.

3. The light applicator system according to claim 1, further comprising a stop defining a maximum pre-piercing depth of the pre-piercing aid.

4. The light applicator system according to claim 3, wherein the pre-piercing aid is integrated into the light applicator, wherein the needle tip of the pre-piercing aid is a needle tip of the light applicator which is arranged at least partially distally of the actively light-emitting element and tapers distally to a point and has a light-transparent scattering body for scattering the light of the actively light-emitting element, wherein the stop is positionable and/or shaped in such a way that the stop defines a maximum pre-piercing depth of the light applicator in a stop position and permits a greater penetration depth of the light applicator in a nonstop position.

5. The light applicator system according to claim 1, wherein the needle tip of the light applicator, with respect to the at least one receptacle of the positioning element, is guided axially centred in the at least one receptacle since an outer diameter of the insertion portion of the light applicator or an outer diameter of an adapter sleeve matching the outer diameter of the insertion portion is adapted to an inner diameter of the receptacle, and wherein the needle tip of the pre-piercing aid, with respect to the at least one receptacle, is guided axially centred in the receptacle since an outer diameter of the pre-piercing aid shaft or an outer diameter of an adapter sleeve matching the outer diameter of the pre-piercing aid shaft is adapted to the inner diameter of the receptacle.

6. The light applicator system according to claim 1, wherein the insertion portion of the light applicator comprises a needle tip, arranged at least partially distally of the actively light emitting element and tapering distalwards to a point, with a light-transparent scattering body for scattering the light of the actively light-emitting element.

7. The light applicator system according to claim 1, wherein the needle tip of the pre-piercing aid has one or more cutting edges.

8. The light applicator system according to claim 7, wherein at least one of the cutting edges is formed by a distally projecting cutting blade.

9. The light applicator system according to claim 1, wherein the pre-piercing aid comprises the pre-piercing aid shaft that has an axial length L1 and a diameter D1 defining a first length-to-diameter ratio L1/D1, and wherein the insertion portion of the light applicator has an axial length L2 and a diameter D2 defining a second length-to-diameter ratio L2/D2, wherein the second length-to-diameter ratio L1/D1 is substantially greater than the first length-to-diameter ratio L2/D2.

10. The light applicator system according to claim 1, wherein the pre-piercing aid comprises the pre-piercing aid shaft that has a diameter that fits precisely into an inner diameter of the at least one receptacle of the positioning element and is larger than a diameter of the insertion portion of the light applicator, wherein the light applicator system further comprises an adapter sleeve, the inner diameter of which corresponds in a precisely fitting manner to the diameter of the insertion portion of the light applicator and which has, at least in portions, an outer diameter which fits precisely into an inner diameter of the at least one receptacle of the positioning element.

11. The light applicator system according to claim 1, wherein an adapter sleeve functions as a protective sleeve of a needle tip of the insertion portion of the light applicator and is axially movably and captively coupled to the insertion portion.

12. The light applicator system according to claim 1, wherein the pre-piercing aid comprises a stabilization sleeve which is axially movable on the pre-piercing aid shaft of the pre-piercing aid and is fixable in a selectable axial position on the pre-piercing aid shaft.

13. The light applicator system according to claim 1, wherein the pre-piercing aid and/or the light applicator has a handle element on the proximal side for manual positioning and orientation.

14. The light applicator system according to claim 13, wherein the axial position of the pre-piercing aid and/or the insertion portion relative to the positioning element is manually adjustable by positioning the handle element in the axial direction.

15. The light applicator system according to claim 13, further comprising a stop defining a maximum pre-piercing depth of the pre-piercing aid, wherein the handle element forms the stop and is axially movable on the pre-piercing aid and/or the insertion portion and is fixable in a selectable axial position.

16. The light applicator system according to claim 1, further comprising a resistance component which exerts a proximal resistance force against a force applied distally manually to the pre-piercing aid up to a maximum resistance force and abruptly releases the pre-piercing aid distalwards upon the distal manual force on the pre-piercing aid exceeding the maximum resistance force.

17. The light applicator system according to claim 16, wherein the resistance component is at least partially elastically resiliently deformable and tensionable by the distal manual force.

18. The light applicator system according to claim 16, wherein the resistance component comprises at least one substantially axially extending spring leg with foot, wherein the foot is radially pushed away by the distal manual force under tension of the spring leg and snaps back under abrupt relaxation of the spring leg when the maximum resistance force is exceeded.

\* \* \* \* \*